US 7,897,924 B2

(12) United States Patent
Xu et al.

(10) Patent No.: US 7,897,924 B2
(45) Date of Patent: Mar. 1, 2011

(54) BEAM SCANNING IMAGING METHOD AND APPARATUS

(75) Inventors: Jingzhou Xu, Ann Arbor, MI (US); Gyu Cheon Cho, Ann Arbor, MI (US)

(73) Assignee: Imra America, Inc., Ann Arbor, MI (US)

( * ) Notice: Subject to any disclaimer, the term of this patent is extended or adjusted under 35 U.S.C. 154(b) by 37 days.

(21) Appl. No.: 12/055,063

(22) Filed: Mar. 25, 2008

(65) Prior Publication Data

US 2008/0251720 A1  Oct. 16, 2008

Related U.S. Application Data

(60) Provisional application No. 60/907,639, filed on Apr. 12, 2007.

(51) Int. Cl.
*G01J 5/02* (2006.01)
(52) U.S. Cl. .................................. 250/341.1
(58) Field of Classification Search ............... 250/341.1
See application file for complete search history.

(56) References Cited

U.S. PATENT DOCUMENTS

| | | | |
|---|---|---|---|
| 4,733,609 A * | 3/1988 | Goodwin et al. | 102/213 |
| 5,048,904 A | 9/1991 | Montagu | |
| 5,168,386 A | 12/1992 | Galbraith | |
| 5,237,444 A | 8/1993 | Schermer | |
| 5,623,145 A | 4/1997 | Nuss | |
| 5,710,430 A * | 1/1998 | Nuss | 250/358.1 |
| 6,242,740 B1 | 6/2001 | Luukanen et al. | |
| 6,815,683 B2 * | 11/2004 | Federici et al. | 250/341.1 |
| 6,909,094 B2 | 6/2005 | Tran et al. | |
| 6,909,095 B2 | 6/2005 | Tran et al. | |
| 6,943,742 B2 | 9/2005 | Holly | |
| 7,274,451 B2 * | 9/2007 | Bustamante et al. | 356/399 |
| 7,449,695 B2 * | 11/2008 | Zimdars et al. | 250/341.8 |

(Continued)

FOREIGN PATENT DOCUMENTS

WO    WO 02/057750 A2    7/2002

OTHER PUBLICATIONS

Karpowicz et al, "Non-Destructive Sub-THz CW Imaging," 2005, Proceedings of SPIE, vol. 5727, pp. 132-142.*

(Continued)

*Primary Examiner*—David P Porta
*Assistant Examiner*—Kiho Kim
(74) *Attorney, Agent, or Firm*—Sughrue Mion, PLLC

(57) ABSTRACT

An imaging apparatus uses focusing and collecting optics in combination with steering optics for efficient imaging of a target using an extended terahertz electro-magnetic range challenged by weak sources and low sensitivity of detection. By proper location of optics to utilize angular conversion of the beam to a lateral scan, a rastering imaging apparatus is demonstrated without moving target or entire imaging system. In at least one embodiment a mirror-lens set is used to steer the terahertz (THz) beam along and (or) to collect the THz beam from each point of the target. The target is imaged with a much higher speed than when moving the target or the entire imaging system. A THz wave image can be taken at video frequency for practical usage of the apparatus in diverse application areas, where it has not been considered to be feasible.

33 Claims, 28 Drawing Sheets

U.S. PATENT DOCUMENTS

| | | | |
|---|---|---|---|
| 7,633,036 B2 | 12/2009 | Gross | |
| 7,633,663 B2 | 12/2009 | Hirakawa | |
| 7,643,869 B1 * | 1/2010 | Dabiri et al. | 600/476 |
| 2003/0066968 A1 * | 4/2003 | Ziolo | 250/341.1 |
| 2003/0149346 A1 * | 8/2003 | Arnone et al. | 600/309 |
| 2005/0161444 A1 | 7/2005 | Kitai et al. | |
| 2005/0230625 A1 * | 10/2005 | Zhang et al. | 250/341.1 |
| 2006/0049356 A1 * | 3/2006 | Shen et al. | 250/341.1 |
| 2006/0176912 A1 * | 8/2006 | Anikitchev | 372/9 |
| 2007/0235658 A1 * | 10/2007 | Zimdars et al. | 250/390.07 |
| 2007/0242274 A1 * | 10/2007 | Cluff | 356/445 |

OTHER PUBLICATIONS

Dickinson et al., "Terahertz imaging of subjects with concealed weapons," 2006, Proceedings of SPIE, vol. 6212, 62120Q.*

Liu et al., "Rapid scanning all-reflective optical delay line for rea-time optical coherence tomography," 2004, Optics Letters, vol. 29, No. 1, pp. 80-82.*

Verghese et al., "Generation and detection of coherent terahertz waves using two photomixers," 1998, Applied Physics Letters, vol. 73, No. 26, pp. 3824-3826.*

A. W. Lee et al, "Real-Time, Continuous—Wave Terahertz Imaging by Use of a Microbolometer Focal-plane Array", Optics Letters, Vo. 30, No. 19, Oct. 1, 2005 pp. 2563-2565.

J. Xu et al, "Terahertz Wave Reciprocal Imaging", Applied Physics Letters 88, Apr. 2006, pp. 151107-1-1151107-3.

Q.Wu et al, "Twp-Dimensional Electro-Optic Imaging of THz Beams", Applied Physics Letters 69, Aug. 19, 1996, pp. 1026-1028.

S. Thibault et al.; "Telecentric scanner for 3D profilometry of very large objects", Proceedings of SPIE vol. 3100, p. 206 (1997).

T. Goyette et al., "1.56 Terahertz 2-frames per second standoff imaging," SPIE OPTO SPIE Photonics West, Jan. 2008 vol. 6893.

N. Karpowicz et al., "Comparison between pulsed terahertz time-domain imaging and continuous wave terahertz imaging," Semiconductor Science and Technology, 20, S293-S299, (2005).

N. Karpowicz et al. , "Continuous-wave terahertz imaging for non-destructive testing applications," IEEE THz Technology, Ultrafast Measurements and Imaging paper TC5-20, p. 329 IEEE 2005.

Löffler et al. , "Continuous-wave terahertz imaging with a hybrid system," Applied Physics Letters vol. 90, paper 091111 2007.

European Search Report Apr. 14, 2010 on EP08006455.3 / 1980817 (EP related case to current application-U.S. Appl. No. 12/055,063.

* cited by examiner

BEAM SCANNING IMAGING METHOD AND APPARATUS

RELATED APPLICATIONS

This application claims priority from U.S. Provisional Application No. 60/907,639 filed Apr. 12, 2007, and incorporates the earlier application by reference herein.

FIELD OF THE INVENTION

This invention relates to imaging technology, and more particularly an imaging process using terahertz electro-magnetic waves. The invention is an apparatus designed for scanning and collecting for the imaging information.

BACKGROUND OF THE INVENTION

Electro-magnetic waves, in the frequency range located between infrared and microwave, are one of the latest developed areas of spectrum. This band is often referred to as the terahertz (THz) band. These waves are transparent for most non-polar dielectrics, such as plastic, paper, stone, wood, oil, smoke, et. al. This makes THz wave imaging an ideal tool as a complement to x-ray and ultrasound imaging in security inspection and quality control applications. Additionally, THz wave imaging provides spectroscopic information on the target, and it can be used to identify the target. THz wave imaging is safe to both the sample and the operator as THz photons have very low energy (meV), which will not ionize molecules.

THz wave imaging technology such as described in U.S. Pat. No. 5,623,145 and U.S. Pat. No. 5,710,430 to M. Nuss, demonstrated the capability of seeing through plastic and mapping metal electrodes underneath. Most THz wave imaging apparatuses developed since then use a raster scanning mode to image the target. THz radiation emitted from the source is focused on the target imaged, and is recorded using a point detector after interacting with the target through transmission or reflection. The target is imaged via scanning the target crossing the THz wave focal spot in an X-Y plane or alternatively scanning the imager in opposite directions. Raster scanning fully utilizes THz waves generated from the source and results in a high measurement dynamic range, which is especially important in the THz regime where lack of intense sources and sensitive detectors pose a problem.

Raster scanning an image requires linearly scanning either the target or the imager within the entire image area, which is not only time consuming but also inconvenient. 2D focal plane imaging, which uses a 2D extended detector (such as an electro-optical (EO) crystal) or a detector array (such as a microbolometer array) instead of a point detector to record the distribution of the THz field at the image plane, was developed to improve imaging speed. An example is reported in "Two-dimensional electro-optic imaging of THz beams," Appl, Phys. Lett., 69, 1026-1028 (1996) by Q. Wu et. al., where a single crystal EO sensor was employed as the extended THz wave sensor. An intense THz beam, which was extended illuminating the entire target, was generated using a femtosecond (fs) laser amplifier through an optical rectification or an optical switching process. The THz wave image of the target was created using an imaging lens and the EO crystal was placed at the image plane. An extended probing beam was used to read out the THz field distribution on the EO crystal, which was the THz wave image of the target.

Detector arrays, and 2D focal plane imaging methods, have also been developed for cw THz radiation under certain circumstances. One example was reported in "Real-time, continuous-wave terahertz imaging by use of a microbolometer focal-plane array," Opt. Lett. 30, 2563-2565 (2005), by A. W. Lee et. al., where a microbolometer array, which was designed for middle infrared radiation, was demonstrated to have the capability to record 2D images at a high THz frequency (2.52 THz). Other examples include U.S. Pat. No. 6,242,740 to A. Luukanen et. al., and U.S. Pat. No. 6,943,742 to S. Holly.

Prior art 2D focal plane THz wave imaging systems, however are only available under limited conditions. Especially, these detector arrays are only sensitive at limited frequency ranges. They also require a relatively more intense THz source than point detectors due to the low sensitivity of detector arrays and dilution of the THz radiation on multi pixels at one time. Alternative methods were therefore developed to improve imaging speed without using an extended detector or detector array. Prior art U.S. Pat. No. 6,909,094 and U.S. Pat. No. 6,909,095, to P. Tran et. al., use a distributed waveguide technique to receive THz wave image at the image plane and using a point detector to receive signals from all pixels sequentially. "Terahertz wave reciprocal imaging," Appl. Phys. Lett. 88, 151107 (2006), by J. Xu et. al, reported using a source array rather than a detector array to present a focal plane image in a reciprocal way. These arts avoid using 2D detector arrays, which are not available or not ideal for THz waves, however there are still other challenges when using a waveguide array or a source array.

U.S. Pat. No. 6,815,683 to J. Federici adapted an interferometric imaging technique from the microwave regime to the THz regime. Using only a few detectors and without using an imaging lens, this technique promises to present large scale THz wave imaging without moving imager or target. On the other had, this art utilizes THz radiation in an inefficient way, as no collection optics is allowed in this technology.

Compared to arts using distributed detection or emission components, the raster scanning method is still the predominantly used imaging method for THz radiation because it provides higher measurement dynamic range, gives better image quality and is available for all kinds of THz wave sources and detectors.

Efforts have also been taken to improve the speed of THz wave raster scanning image. An example was described in WO 02/057750 by B. Cole et. al., where a THz wave was guided into an imaging head, which contains only a limited number of optics (and THz optics). It was the imaging head rather than the entire imager being scanned in then imaging process. The speed of imaging was improved because less mass was scanned.

The detectivity of THz waves currently available is not sufficient to utilize these waves for an imaging device in a comparable fashion to other well developed areas of wavelength ranges. Furthermore, the lack of a strong source to overcome the detectivity problem is also challenging. The immature source technology also leads to difficulties in manipulating the wave to be accommodated into other techniques. As a result, detection of scattered light out of a target to be imaged is not a practical method, due to the lack of strong source. Equally, realization of a modulation technology to enhance the detectivity of a weak source is not feasible due to immature technology surrounding the source. Speed of imaging is another important factor in considering an effective imaging system.

Currently, no prior art is known for an imaging apparatus in the range of extended THz frequencies, e.g., 1 GHz~100 THz, disclosing a concept for realization of practically usable sensitivity and speed. This disclosure addresses these two major points with an exemplary embodiment focusing on two dimensional raster scanning of an image by scanning the THz beam across each spot of the target using a wave in the frequency range of 10 GHz–3 THz.

SUMMARY OF THE INVENTION

The present invention is directed to an scanning image system, in particular a THz wave imaging system. Rastering a target to be imaged with a pulsed THz wave centered at 1 THz is disclosed to be an exemplary embodiment, although the frequency range may be between about GHz and 100 THz. Some embodiments may utilize a frequency range of 1 GHz to about 10 THz. Other embodiments may utilize a frequency range of about 1 GHz to about 20 THz. Corresponding wavelengths may be up to at least a few tens of microns, for example about 20 microns. The THz source of the present THz wave imager could be generated coherently or incoherently.

Sources can be a THz pulse utilizing ultrafast optical rectification or an optical switch in combination with an ultrashort optical pulse laser. Furthermore, a cw THz electronic transmitter, or a THz wave laser, or even an incoherent thermal emitter can be incorporated within this disclosure.

On the other hand, in the detection scheme, a photo-conductive switch, electro-optic sample, bolometric detection, or other devices can be incorporated within the invention. For phase-sensitive detection, often called coherent detection, both pulsed and continuous wave can be combined within this disclosure to utilize the suppression of thermal noise in the detection technique. A time-domain point detector with relatively high response speed, for high speed imaging, is disclosed to be an exemplary embodiment.

Instead of linearly scanning the target or the imager, a mirror/lens set is used for steering the THz beam across each spot of the target. The steering mirror set could be driven using a galvanometer (or a pair of galvanometers for 2D scanning), which supports a line scanning speed up to 300 Hz (up to 600 lines per second with a zigzag scanning mode). This speed is sufficient for a real time imaging application. Especially, the incident beam could be collimated and the steering mirror could rotate about two axes, whose crossing point locates at a focal point of the focusing lens. The target is located at the focal plane on the opposite side of the imaging lens and is normal to the optical axis of the lens. Under this condition, the THz beam will be retro-reflected by the target and full THz radiation will be utilized in the imaging process.

The imaging wave can be obtained primarily by reflection or transmission. However, scattering or refraction arranged to a specular direction can be incorporated into the invention. Alternatively, the present invention could be used in a passive imaging configuration, where no incident THz radiation is required and the mirror/lens set is used to steer THz radiation emitted or reflected from an external source not included in the imaging system from each spot of the target to the point detector.

The spectral information carried by reflection, transmission, emission, refraction and scattering is analyzed by a time-domain measurement.

DETAILED DESCRIPTION OF THE PREFERRED EMBODIMENTS

Figure 1:
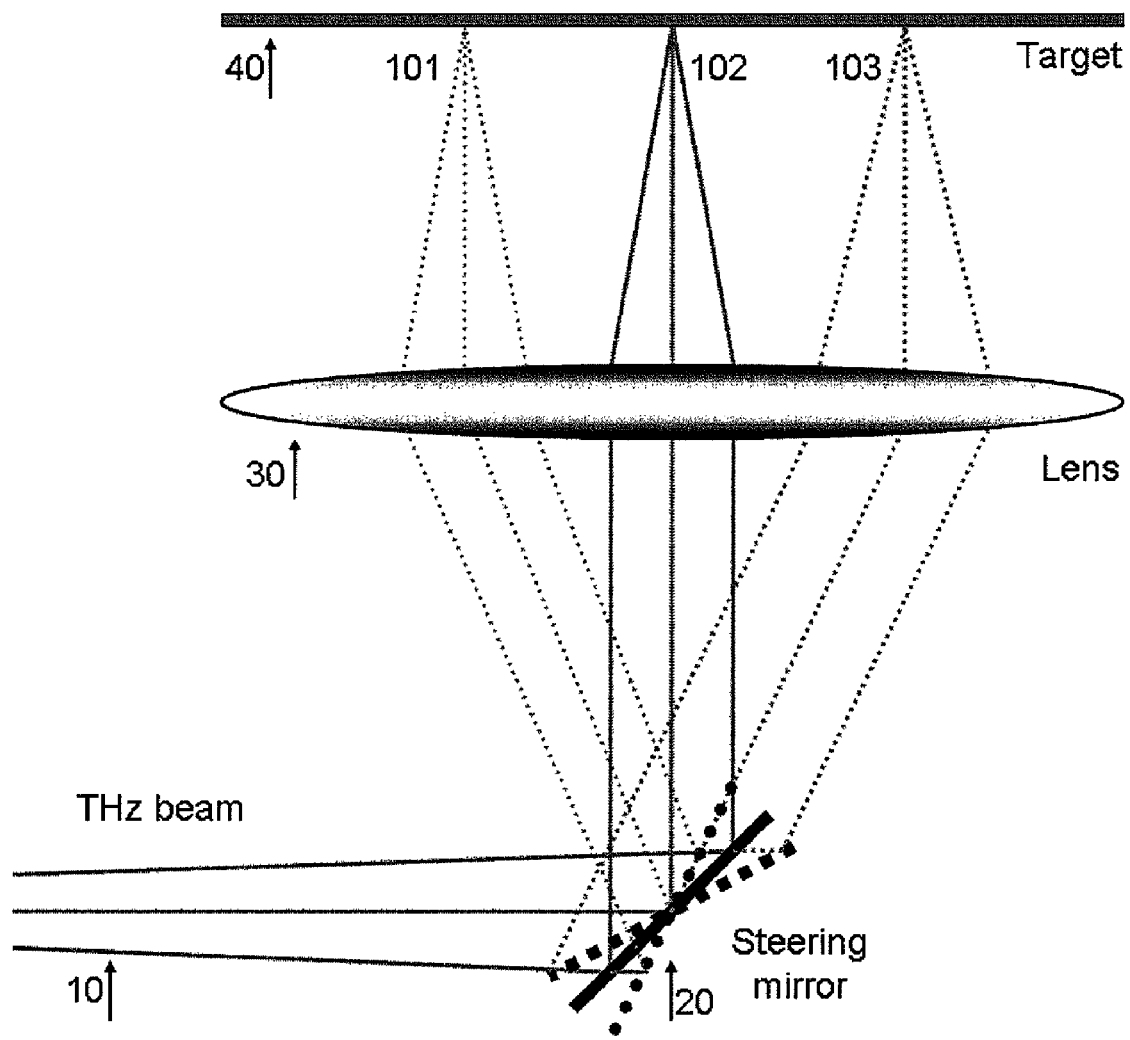
FIG. 1 is a diagram of a first embodiment of the invention.

FIG. 1 represents an exemplary embodiment of the present invention. A THz incident beam 10 is guided by a steering mirror 20 incident onto a focusing lens 30 and it is focused by the lens 30 onto the target 40. Rotating the mirror 20 scans the focal spot to different locations (101, 102, and 103 et. al.) on the target. The THz beam having interacted with the target (either transmission through or reflection from) will be collected and fed into a point detector. The image of the target will be created by rotating the steering mirror 20. The focusing lens 30 could be made using polyethylene, silicon, et. al.

Furthermore, a curved mirror such as paraboloidal mirror can also be incorporated in replacement of the lens, with a proper adjustment of the target location.

Figure 2A:
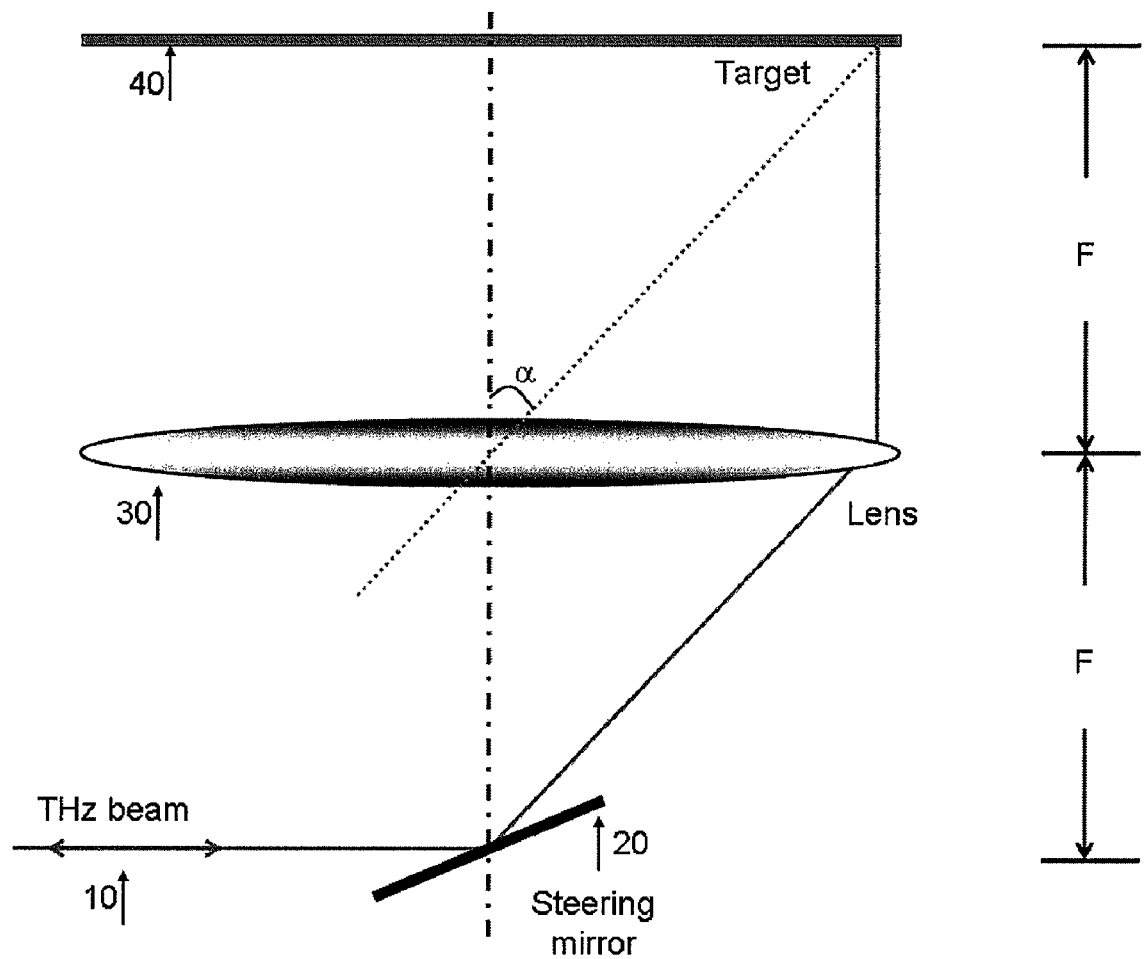
FIG. 2a is a diagram of an embodiment of the invention in a reflection configuration.
Figure 3:
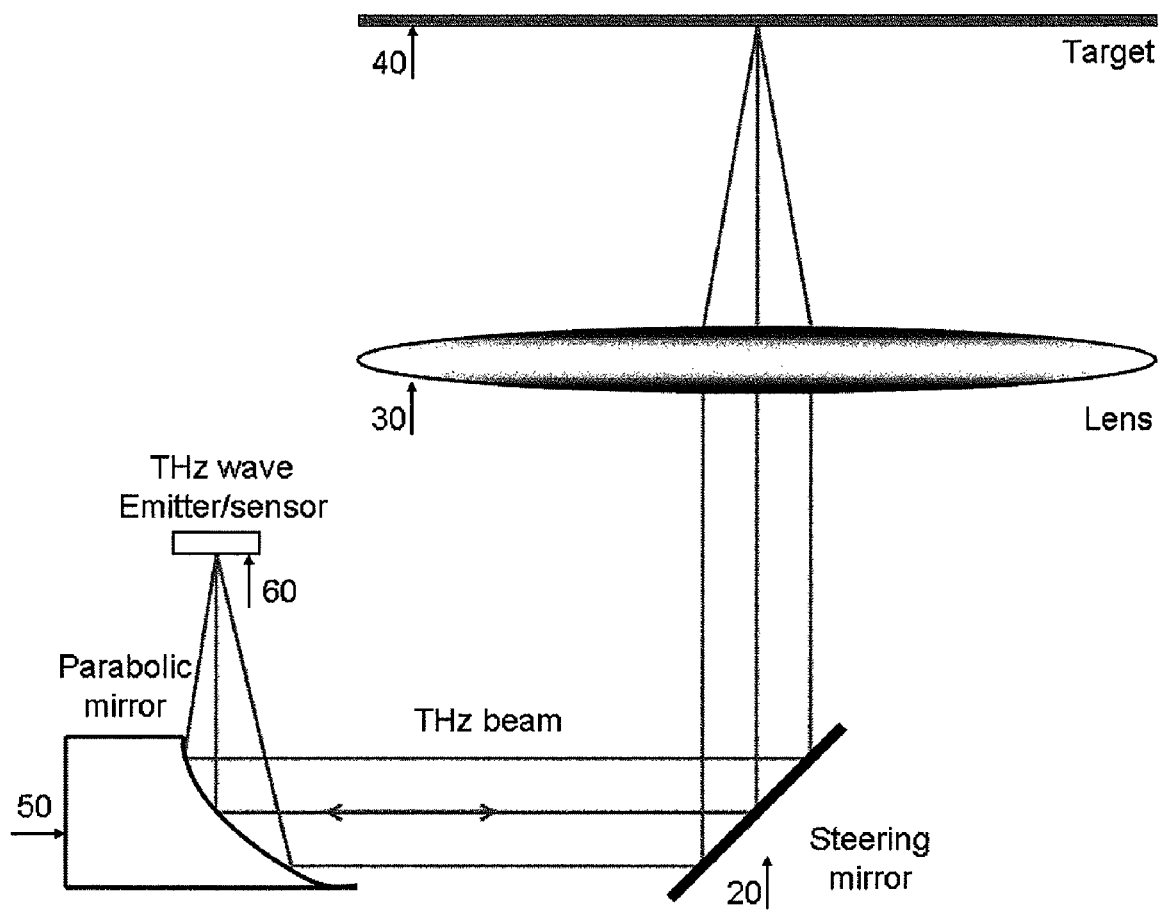
FIG. 3 is a diagram of an embodiment of the invention using a THz wave as its imaging wave.

FIG. 2a shows an important embodiment of the present invention, where a collimated THz beam 10 is incident into the mirror-lens set and it intersects with the rotation axis of the steering mirror 20 at one focal point of the lens 30. As a collimated THz beam 10 comes from its focal point, the lens 30 focuses the beam normally onto its focal plane on the opposite side. The target 40 lies on the focal plane. Therefore, each spot on the target is a function of the incident angle. If the THz beam is specularly reflected by the target, which is mostly true as THz waves have long wavelength, for example up to at least a few tens of microns, the returning beam counter propagates with the input beam. As a result, the entire radiation transmitted from the source can be utilized to image the target. FIG. 3 is a diagram showing use of this embodiment with a THz wave source and detector. A THz wave transceiver 60 could be used to emit and receive THz waves. THz wave focusing optics such as a parabolic mirror 50 is used to collimate transmitted THz waves, and the same optics can be used to collect returning THz waves.

Figure 2B:
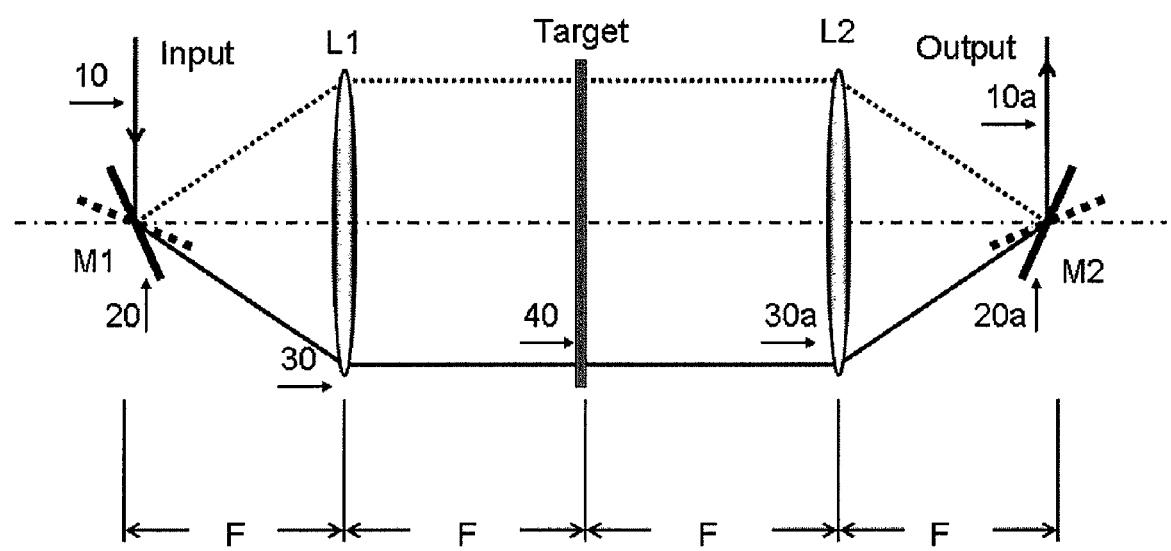
FIG. 2b is a diagram of an embodiment of the invention in a transmission configuration.

The embodiment shown in FIG. 2a can also work in a transmission configuration as presented in FIG. 2b. In FIG. 2b a receiving mirror-lens set (20a and 30a) is placed on the other side of the target 40 and it is an image of the incident set (20 and 30). The steering mirror 20a at the receiving side acts as a slave of the incident steering mirror 20. Its rotation is synchronized with the incident mirror 20. As a result, the received THz beam after the steering mirror 20a will be collimated and maintain the same propagation direction at all rotation angles, and a fixed detector will be able to receive the THz beam transmitted through any spot on the target.

Another interesting concept is the measurement of the angular radiation distribution of radiation out of a point source if the incident light is replaced with the radiation out of the target itself.

Furthermore, the focusing lens, which is identical to the collecting optics, can move along the optical axis, so that information to be imaged can be obtained at the surface or inside the target, if the target is sufficiently transparent.

The wave to be imaged can be extended in its property beyond the reflection shown in this exemplary embodiment. As long as the geometry of the focusing and collecting optics together with the steering optics is fulfilled as described in earlier sections, the origin of the wave out of the target can be scattered in the specular direction, or diffracted or even refracted to the specular direction by the structure in or on the sample. Randomly distributed nano-structures on and inside the target can be an example of an arrangement where this is possible.

It should be noted that, all embodiments discussed above and hereafter can be easily modified for use in a passive imaging configuration. The simplest modification is just replacing the transmitter with a point receiver. Rotating the steering mirror 20, THz radiation emitted (reflected) from each spot of the target 40 will be guided into the receiver sequentially.

The diameter of the imaging area in embodiments shown in FIG. 2a and FIG. 2b is:

$$D_I = 2F \tan(\alpha), \tag{1}$$

where F is the focal length of the focusing lens 30 and $\alpha$ denotes the maximum beam spanning angle driven by the steering mirror 20. In most cases, the THz beam spanning angle is two times the steering mirror's rotating angle.

Figure 4:
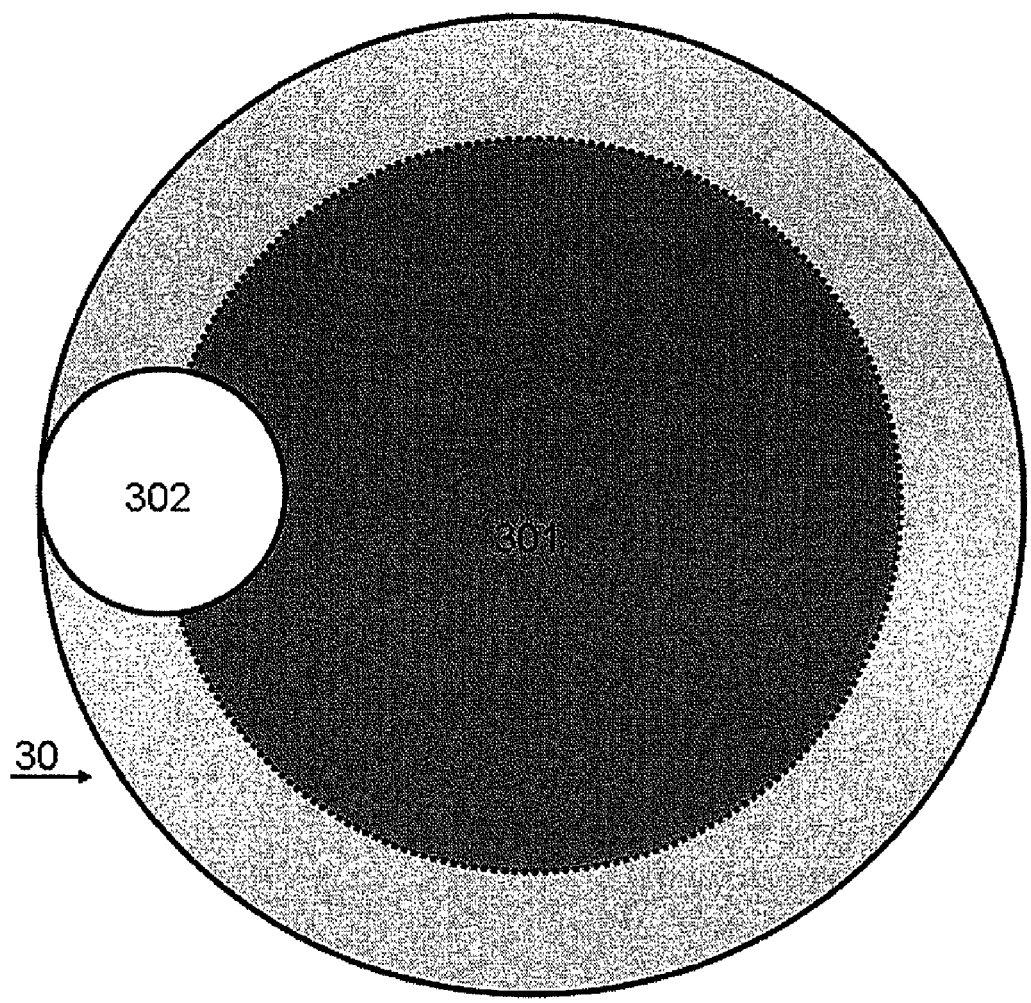
FIG. 4 indicates the imaging area in the embodiment presented in FIG. 3.

On the other hand, the maximum image size is also limited by the size of the focusing lens and the size of the THz beam. In FIG. 4, the bigger solid circle shows the boundary of the focusing lens 30 and the smaller open circle 302 is the THz beam on the lens. The maximum offset of the THz beam on the focusing lens is presented in FIG. 4. If the spanning angle is even bigger, part of the THz beam will be outside of the imaging lens. The dashed circle 301 indicates the maximum imaging area determined by the imaging lens and THz beam. The diameter is:

$$D_I = D_L - D_B, \tag{2}$$

where $D_L$ and $D_B$ are diameters of the focusing lens 30 and the THz beam 302, respectively.

The spatial resolution of such an image is limited by the diffractive limitation of the THz beam:

$$\Lambda = F\lambda/D_B, \tag{3}$$

where $\lambda$ is wavelength of the imaging wave. To keep the same spatial resolution and scanning angle while obtaining a larger imaging area, one needs to scale up the size of the lens, its focal length, and the diameter of the THz beam on the lens.

Figure 5A:
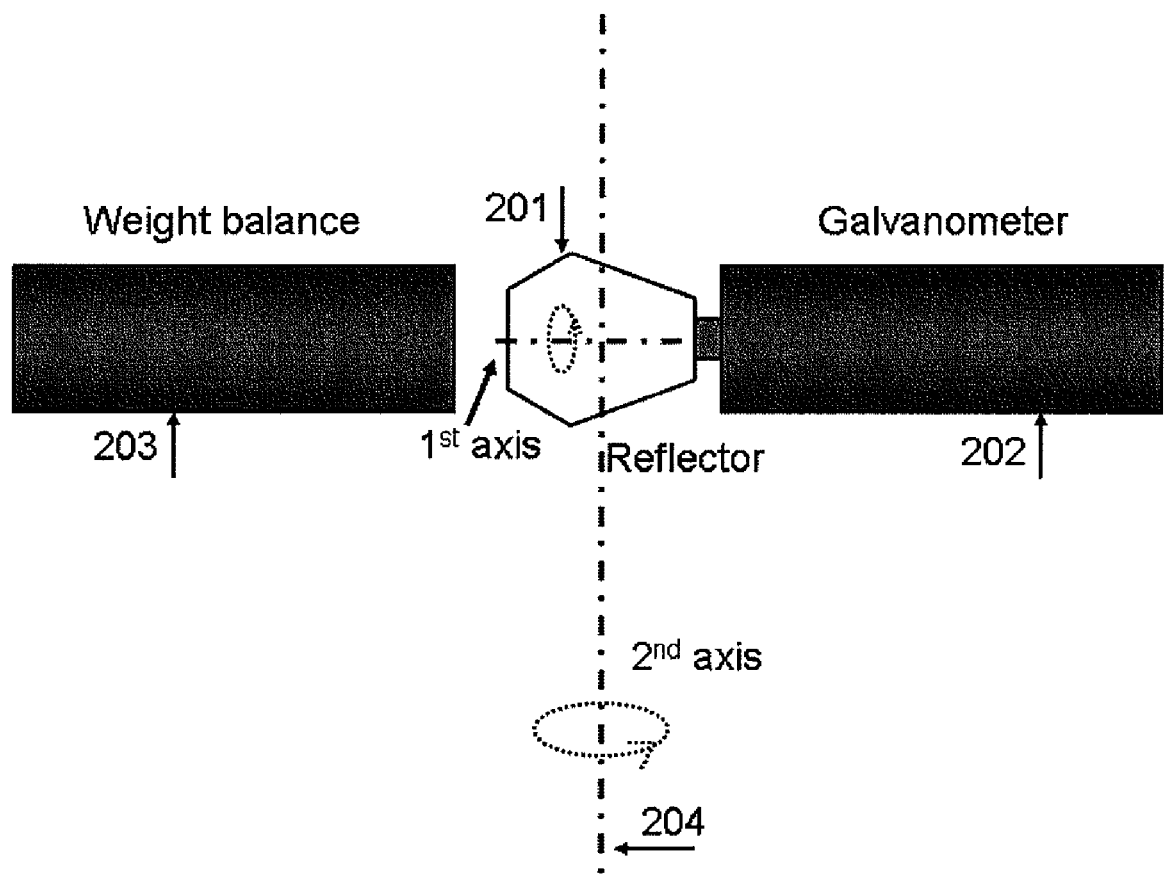
FIG. 5a is a diagram of a steering mirror setup in one embodiment of the invention.
Figure 5B:
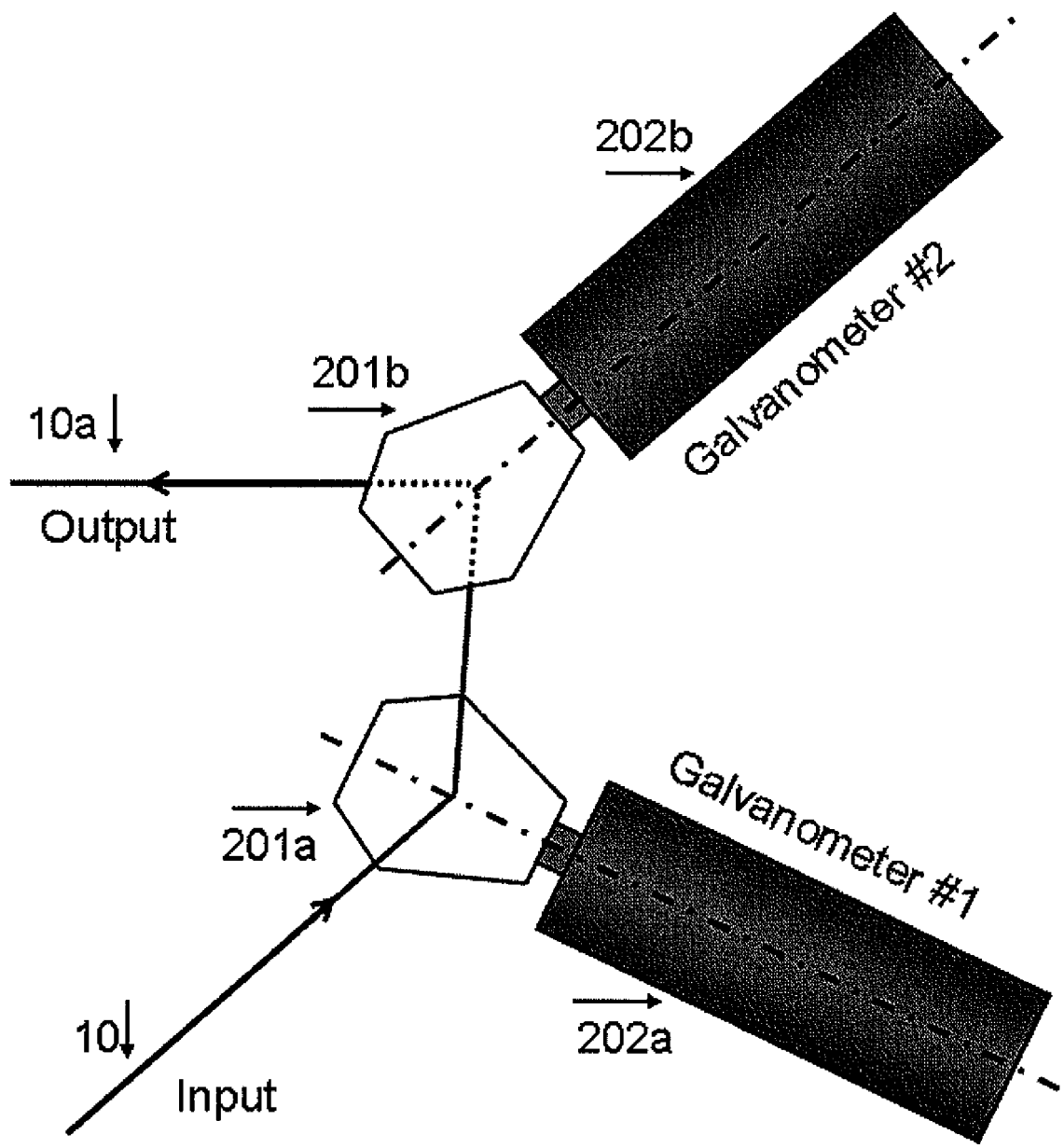
FIG. 5b is a diagram of another steering mirror setup in one embodiment of the invention.

FIG. 5a and FIG. 5b give two examples of the steering mirror scanning setup 20. In FIG. 5a, one galvanometer 202 is used to drive the steering mirror 201. It steers the THz beam spanning one dimension and the entire setup (201, 202, and 203) is rotated about another axis 204 perpendicular to the first one. The cross point of these two axes is located at the focal point of the focusing lens 30 shown in FIG. 2. 2D scanning can also be made using a configuration shown in FIG. 5b, where one galvanometer 202a scans the THz beam along one dimension and the other galvanometer 202b scans the THz beam along the perpendicular direction.

Figure 6A:
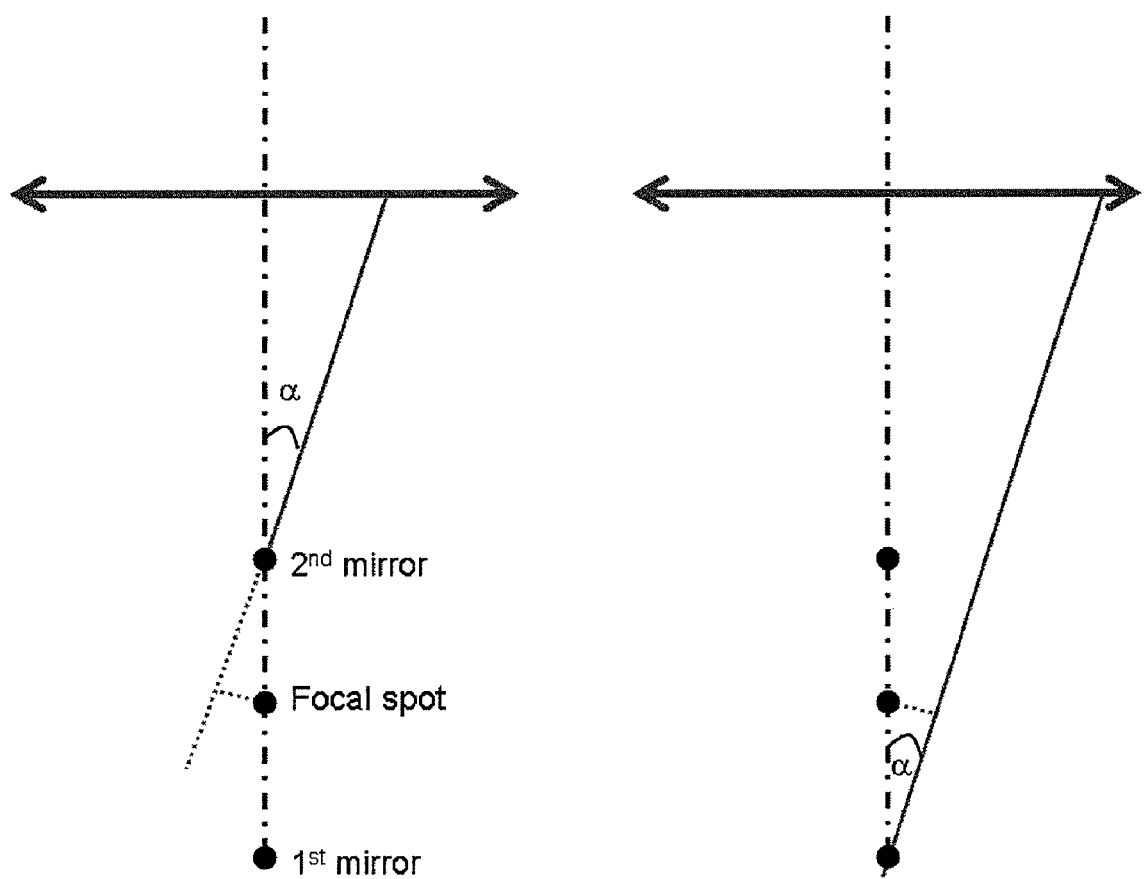
FIG. 6a indicates parallel beam walking for two different mirrors at different sides of the focal point in FIG. 5b.

The configuration shown in FIG. 5b is more compact and is freely controllable in either scanning dimension. However it should be noted that the two-galvanometer configuration may introduce parallel beam walking into the beam scanning apparatus. As presented in FIG. 6a, there are two rotation axes, which present the first mirror 201a (actually it is the image of the $1^{st}$ mirror 201a in the $2^{nd}$ mirror 201b) and second mirror 201b respectively. When setting the focal spot in the middle between the first and second mirrors, the THz beam is displaced from the focal point of the focusing lens, and its scanning ranges on the lens 30 are different when scanning the first mirror and the second mirror for the same angle.

Figure 6B:
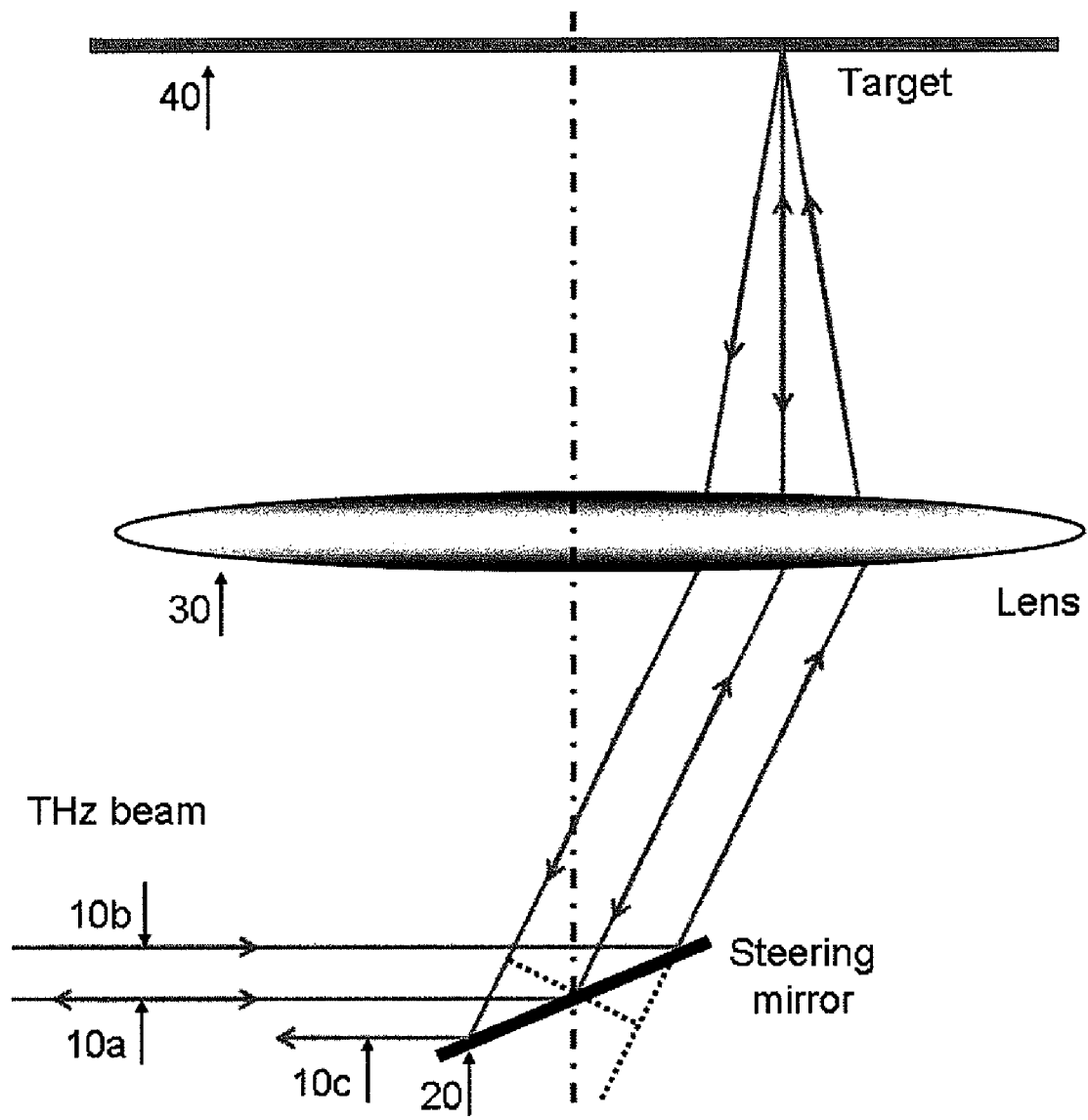
FIG. 6b shows beam traces when the incident beam has a displacement to the focal point.

FIG. 6b shows beam traces of THz beams with a certain incident angle. If the incident THz beam (10a) passes through the focal spot of the focusing lens 30, the beam is bent by the lens 30 normally incident onto the target 40. The target then retro-reflects the incident beam. If the incident beam (10b) is away from the focal point with a displacement of H, the returning beam will be on the opposite side of the focal point with a counter propagation direction and will have the same displacement to the focal point. Consequently, the returning beam will be collected by the same focusing optics (such as 50 in FIG. 3) and focused to the detector at the same spot although there is parallel beam walking. As a result, the parallel beam walking will not mislead the returning beam. If the image area is 30 mm in diameter and the focal length of the imaging lens is 50 mm, the maximum scanning angle is +/−16.7°. In this case, if the distance between the $1^{st}$ and the $2^{nd}$ mirror is 25 mm, the maximum beam walking will be 8 mm.

Figure 6C:
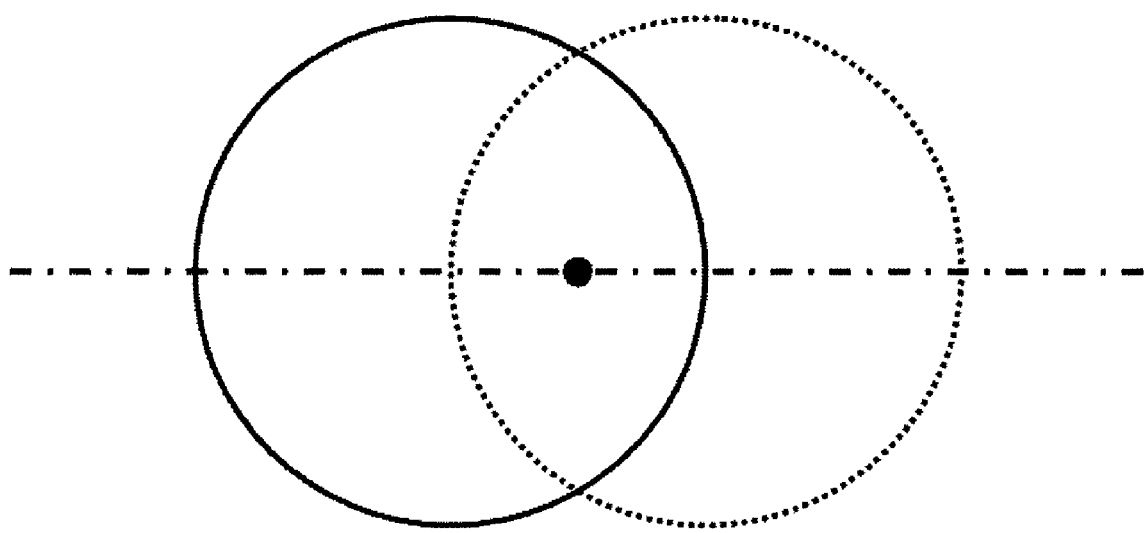
FIG. 6c indicates returning beam spots from the incident one on the steering mirror.

Although parallel beam walking does not mislead the returning beam, it does reduce overlap between the returning beam and the input beam. FIG. 6c shows the overlap of these two beams. The solid circle represents the input beam, which can be considered as the aperture of the steering mirror. The dashed circle is the returning beam, which is symmetric with the input beam about the focal point shown as a solid spot in the figure. Because the center of the input beam is off from the focal point, part of the returning beam lies outside of the steering mirror. As a result the collection efficiency of the returning beam is reduced.

Figure 7:
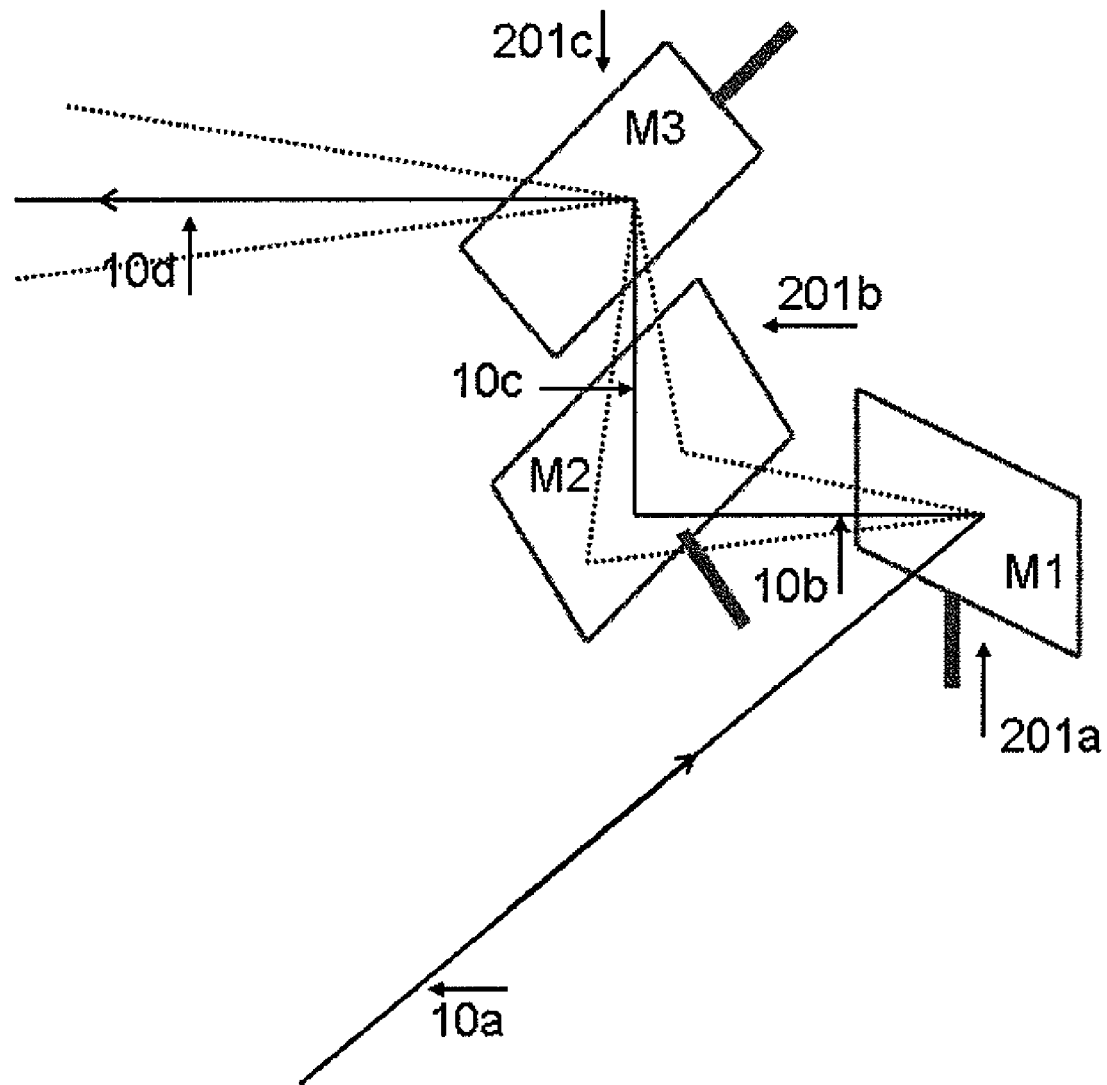
FIG. 7 is a diagram of one embodiment of the invention using three steering mirrors.

A galvanometer setup with three galvanometers can be used to create 2D beam scanning and to compensate the parallel beam walking in the apparatus. An exemplary embodiment is presented in FIG. 7. The incident beam $10a$ is scanned by the first steering mirror $201a$ in horizontal direction ($10b$). A second steering mirror $201b$, which rotates according to the first mirror $201a$, is used to maintain the beam spot on the third steering mirror $201c$ at the same location while the mirror $201a$ is scanning. Rotation of mirror $201a$ and $201b$ results in the THz beam scanning in a horizontal direction starting from a single spot on mirror $201c$. The steering mirror $201c$ rotates in the vertical direction. Therefore, using three steering mirrors ($201a$, $201b$ and $201c$), the THz beam is scanned in 2D bending from a single point.

Figure 8A:
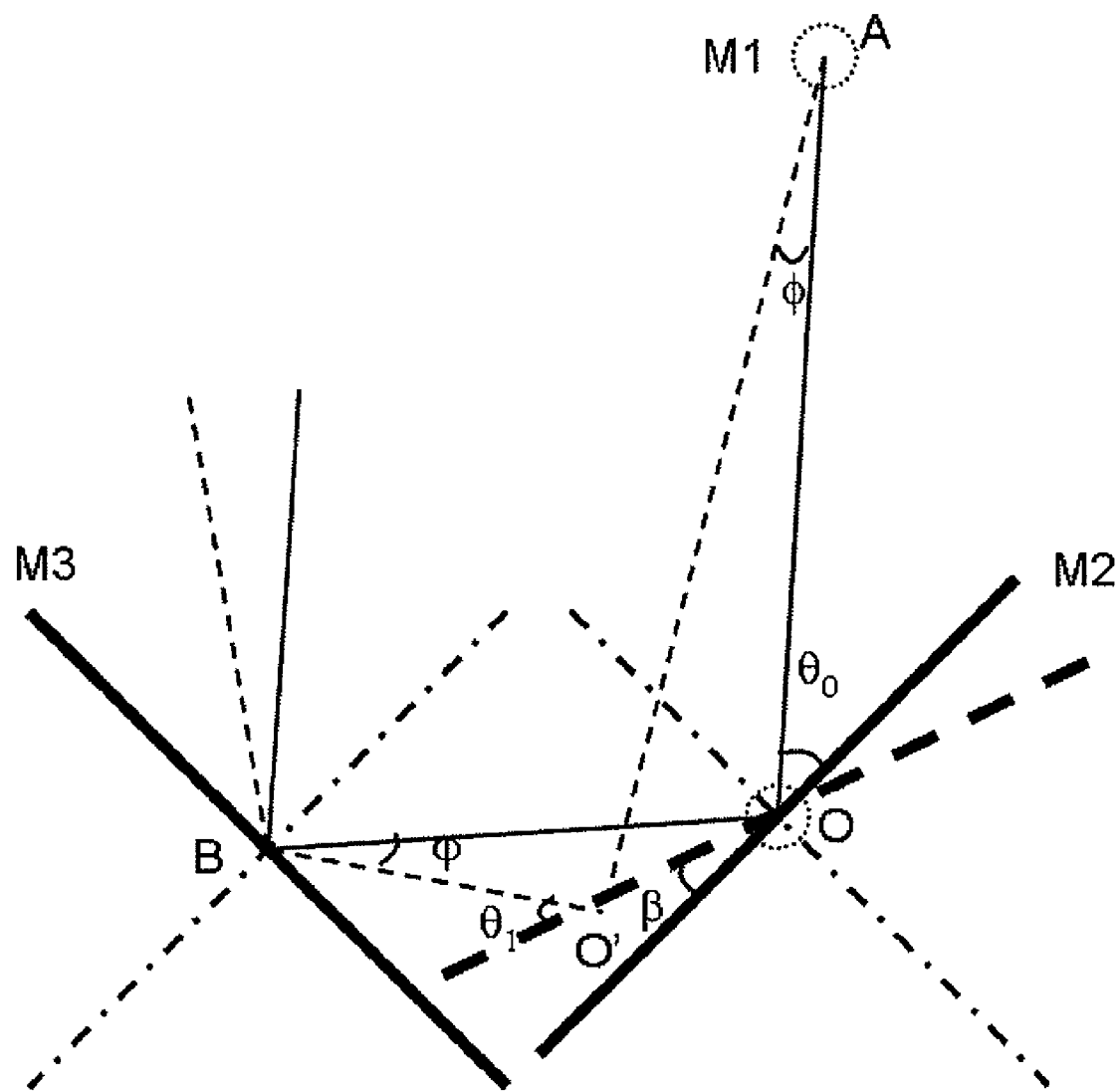
FIG. 8a shows beam traces in the 3-mirror configuration.

FIG. 8a gives the relationship between rotation angles of the first steering mirror and the second steering mirror. The incident beam is guided into the steering mirror set at the point A, which is the rotation center of the $1^{st}$ mirror. The rotation center of the $2^{nd}$ mirror is at O. When the $1^{st}$ mirror is at its original position, the input beam is steered following AO, and it will be reflected by the $2^{nd}$ mirror to the $3^{rd}$ mirror following OB, where B is located on the rotation axis of the $3^{rd}$ mirror. For any angle of $\phi$, which the incident beam changes from its original direction steered by the $1^{st}$ mirror, there is an angle of $\beta$. If the $2^{nd}$ mirror rotates $\beta$, the incident beam follows the path of AO'B, and ends at the same point B on the $3^{rd}$ mirror. Rotation of the $1^{st}$ mirror and the $2^{nd}$ mirror together results in a scanning angle $\phi$ of the output beam. $\beta$ and $\phi$ as functions of $\phi$ are in Eq. 4.

$$\frac{\sin\varphi}{\sin\phi} = \frac{AO}{BO}, \qquad (4)$$

$$\beta = (\phi + \varphi)/2$$

Another important feature of this configuration is the beam walking distance on the $2^{nd}$ mirror, which determines the size of the second mirror.

$$OO'' = \frac{BO\sin\phi}{\sin\theta_1}, \qquad (5)$$

Where $$\theta_1 = \theta_0 + \beta - \phi.$$

Figure 8B:
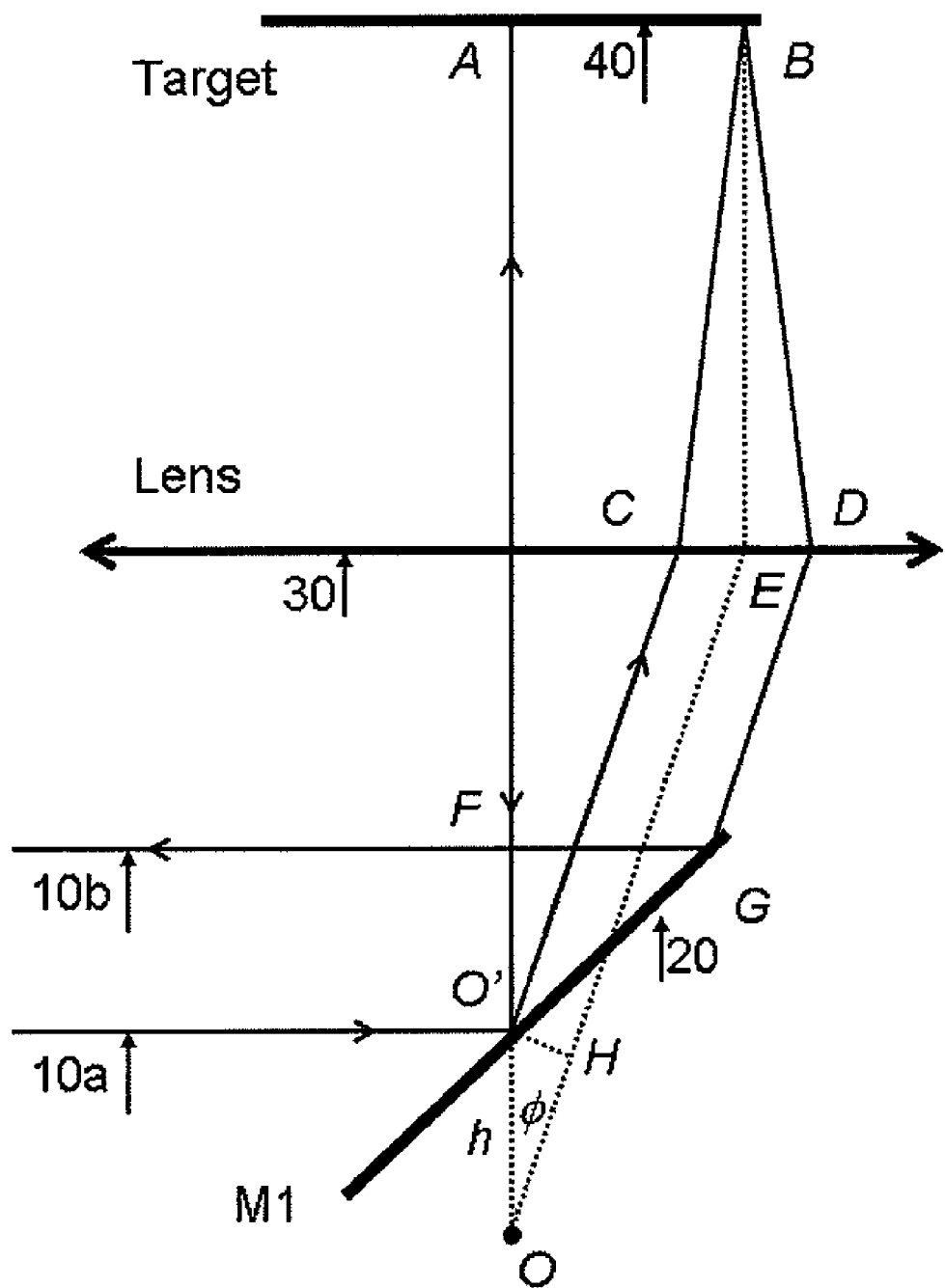
FIG. 8b shows the temporal variation when the steering mirror has offset to the focal point of the focusing lens.

The parallel beam walking can be compensated using a three-galvanometer configuration. However there is another issue created by the beam path changing which must be taken into account, especially when the imaging process has fine temporal resolution, such as in pulsed THz wave imaging. This issue is the optical path variation, which results in a temporal variation in temporal resolved imaging, with beam scanning. FIG. 8b shows the optical path in the apparatus if the rotation center of the steering mirror has a displacement h to the focal point of the focusing lens. Optical path variation as a function of the THz beam scanning angle is:

$$\Delta OP = 2h[1-\cos(\phi)]. \qquad (6)$$

It is positive when the rotation axis is closer to the lens, and is negative otherwise.

Optical path as a function of rotation angle in three-galvanometer configuration can be resolved according to FIG. 8c, as:

$$OP = \frac{AO\sin(\theta_0 + \beta) + BO\sin(\theta_0 - \beta)}{\sin\theta_1} \qquad (7a)$$

If OA=OB=L is satisfied, Eq. 7a can to be simplified as:

$$OP = 2L\cos(\beta), \qquad (7b)$$

Unlike the temporal variation shown in Eq. 6, the temporal variation in this case is determined by the structure of the three-galvanometer setup, and it cannot be minimized by optimizing alignment. When the distance between the $1^{st}$ mirror and the $2^{nd}$ mirror (same as between the $2^{nd}$ mirror and the $3^{rd}$ mirror) is 40 mm, the maximum temporal variation for a 20 degree beam span is 5 mm (33 ps temporal variation).

Figure 9:
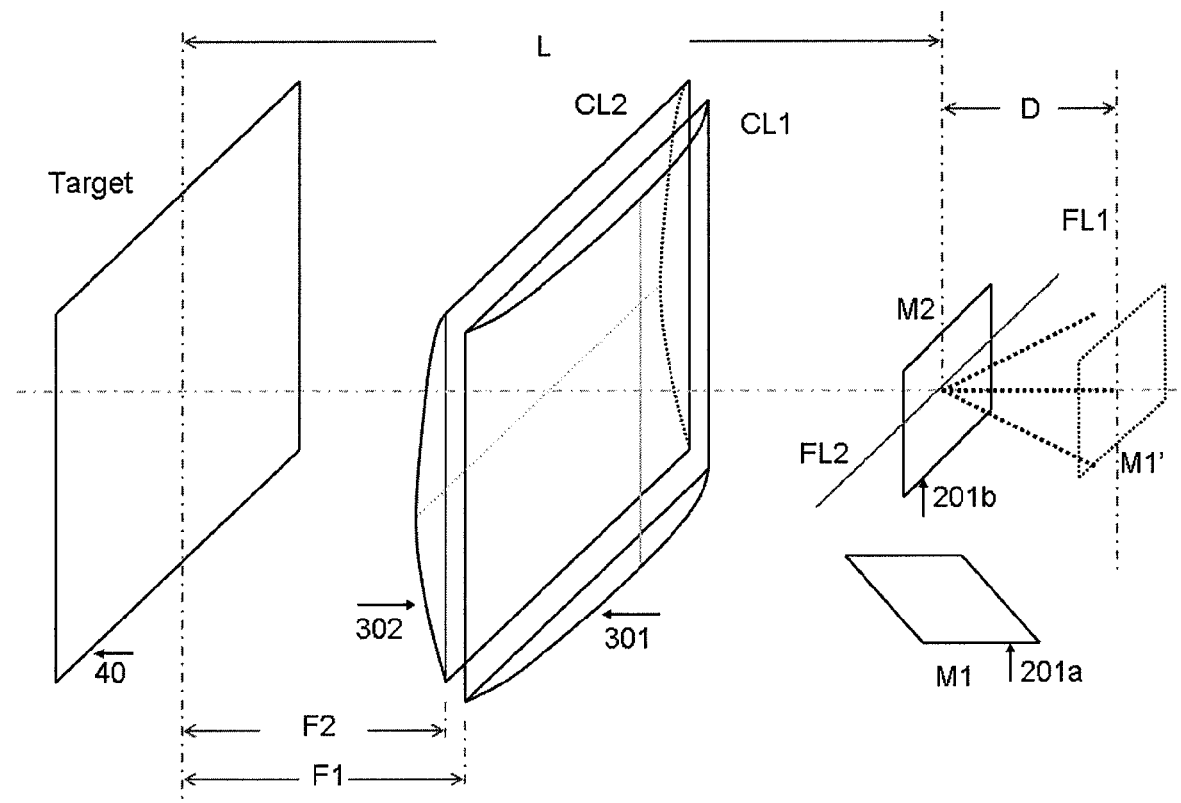
FIG. 9 is a diagram of two cylindrical lenses in one embodiment of the invention.

Temporal variation causes no effect in an imaging process with no temporal resolution, or with a temporal resolution much longer than the temporal variation. However for some imaging processes, which have a fine temporal resolution, such as pulsed THz wave imaging, one needs to retrieve the imaging after recording images at all temporal positions, in order to compensate the temporal variation in scanning. FIG. 9 is a diagram of one embodiment of the present invention used to minimize both parallel beam walking and temporal variation with scanning in a two-galvanometer configuration. In this embodiment, 2 cylindrical lenses 301 and 302 are used to replace the single focusing lens. One optic or optical set, which has different focal length following two different axes, can also be used for this purpose.

Overall, if an oversized target needs to be imaged, the exemplary embodiment described so far can be extended so that the all required optics can be translated laterally together. In this way, imaging of area-by-area is possible. The time for the translation can be utilized for data processing of the area imaged prior to the translation.

M1 and M2 are two scanning mirrors (X-mirror $201a$ and Y-mirror $201b$) driven by a pair of galvanometers. M1' is the image of M1 in M2 in the original direction. CL1 and CL2 are two cylindrical lenses. The focal length of each lens (301 and 302) equals half of the distance between the corresponding mirror ($201a$ for 301, and $201b$ for 302) to the target 40. The distance between the target 40 to each of the cylindrical lens (301 or 302) is the focal length of the lens. CL1 and CL2 focus a collimated beam onto the target, and the lateral position of the focal spot is determined by the direction of the incident beam.

As presented in FIG. 9, when M1 is scanning and M2 is fixed or vice versa the focal spot scans along x or y axes on the target. The beam will be retro-reflected and no temporal shift will occur. When both M1 and M2 are scanning, however, the image of M1 moves with M2's scanning. This causes the beam bending position to leave the focal line of CL1 (FL1 in FIG. 9). A detailed calculation of beam walking and temporal variation is complicated. Eq. 8a and Eq. 8b give approximate estimations of parallel beam walking and optical path variation as functions of the beam scanning angle:

$$\delta = 2D\sin\phi(1-\cos\theta), \qquad (8a)$$

$$\Delta OP = 2\Delta(1-\cos\phi) = 2D(1-\cos\phi)(1-\cos\theta). \qquad (8b)$$

If the distance between M1 and M2 is 25 mm and the maximum scanning angle is +/−20°, the maximum beam walking is 1 mm and maximum optical path variation is 185 μm.

Figure 10:
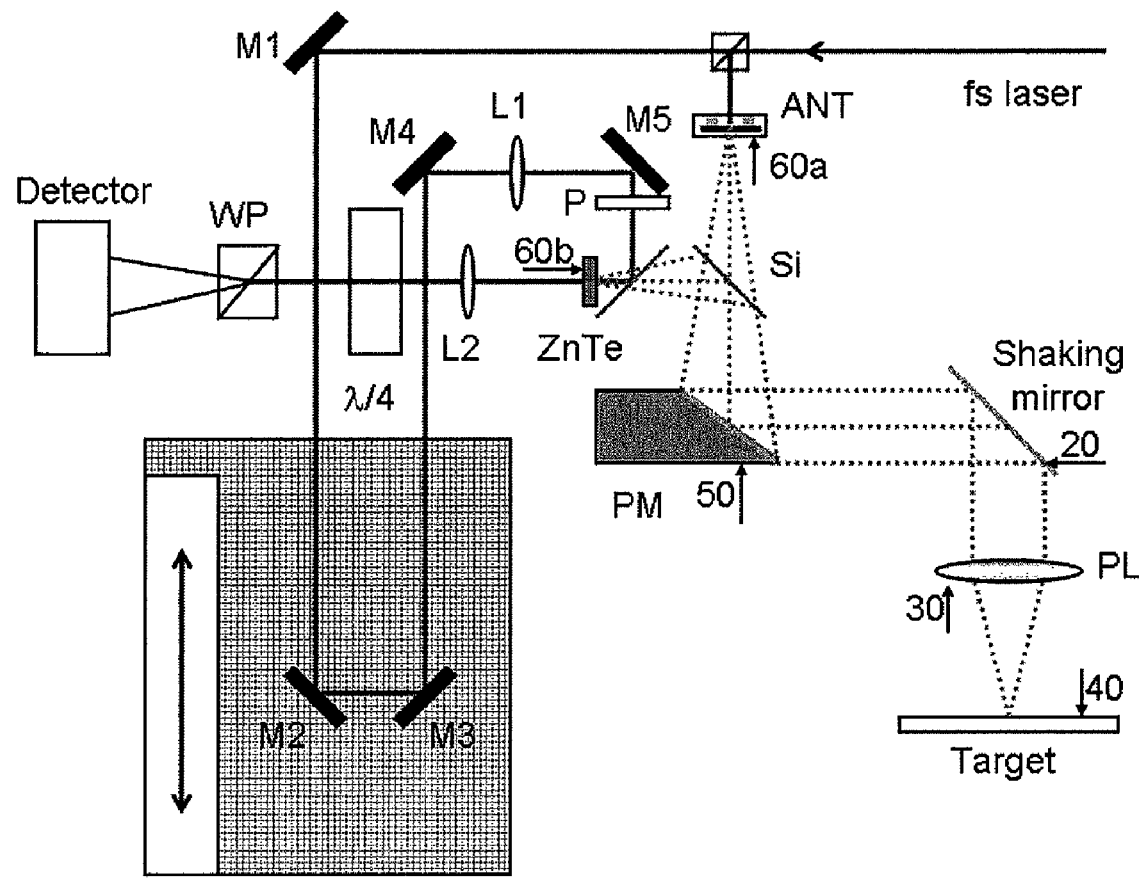
FIG. 10 is a diagram of one embodiment of the invention used in a pulsed THz system.

FIG. 10 is a schematic diagram of a pulsed THz wave apparatus, which was used to verify the concept of the present invention. In this system, a femtosecond (fs) laser (Femtolite F-100) is used to generate THz pulses and to detect them. Firstly, the fs laser beam is split into two arms, the pumping arm and probing arm, respectively. THz pulses are generated via a photoconductive switch 60a triggered by the pumping pulses. Transmitted THz beam is collimated using a parabolic mirror 50 and is guided into a double axis galvanometer set 20. THz beam output from the galvanometer set is focused using two cylindrical lenses 30 onto a target 40. In one experiment, the aperture of the galvanometer is 15 mm in diameter. The displacement between two mirrors of the galvanometer set is 25 mm. Focal lengths of the two cylindrical lenses are 57 mm and 44 mm respectively. The reflected THz beam is picked-up by a silicon beam splitter in the THz beam and part of the reflected THz beam was focused onto a (110) ZnTe crystal 60b, which is used as the sensor of THz pulses. The THz beam and the probing beam collinearly propagate through the ZnTe crystal, where the polarization of the probing beam is modified through an EO process. The THz field is recorded by a polarization sensitive balanced detection geometry afterward.

Figure 11:
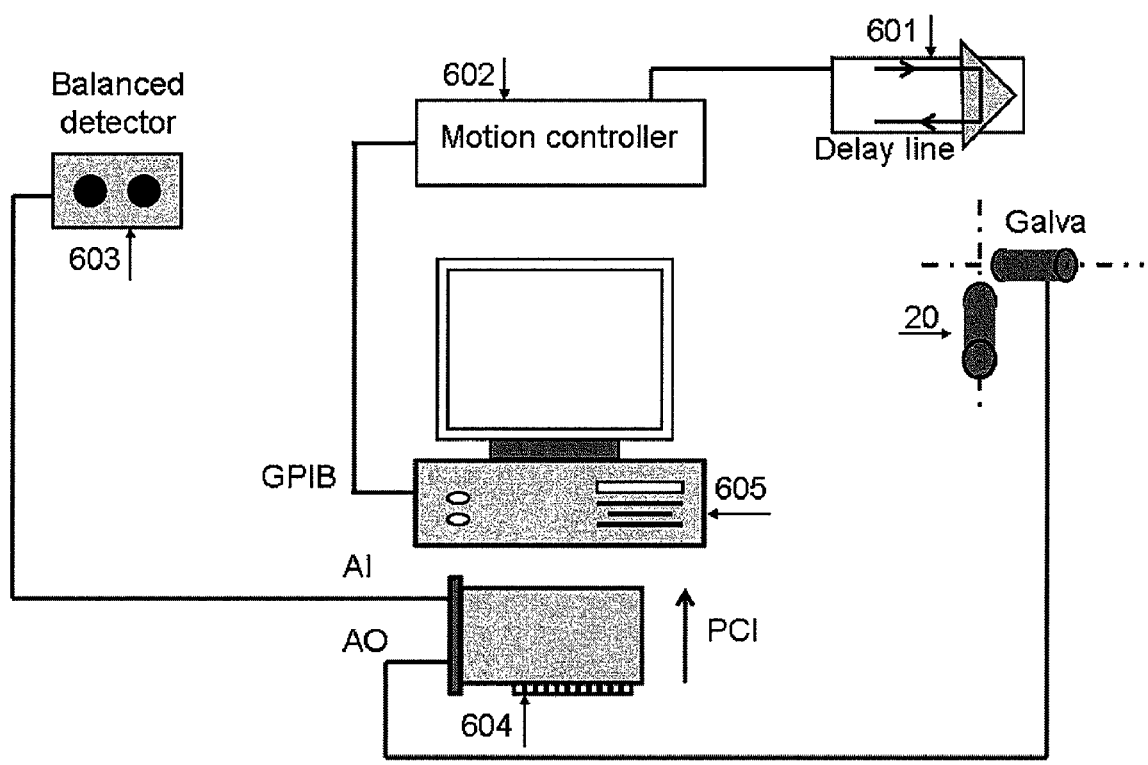
FIG. 11 is a diagram of the control system of the embodiment shown in FIG. 10.
Figure 12:
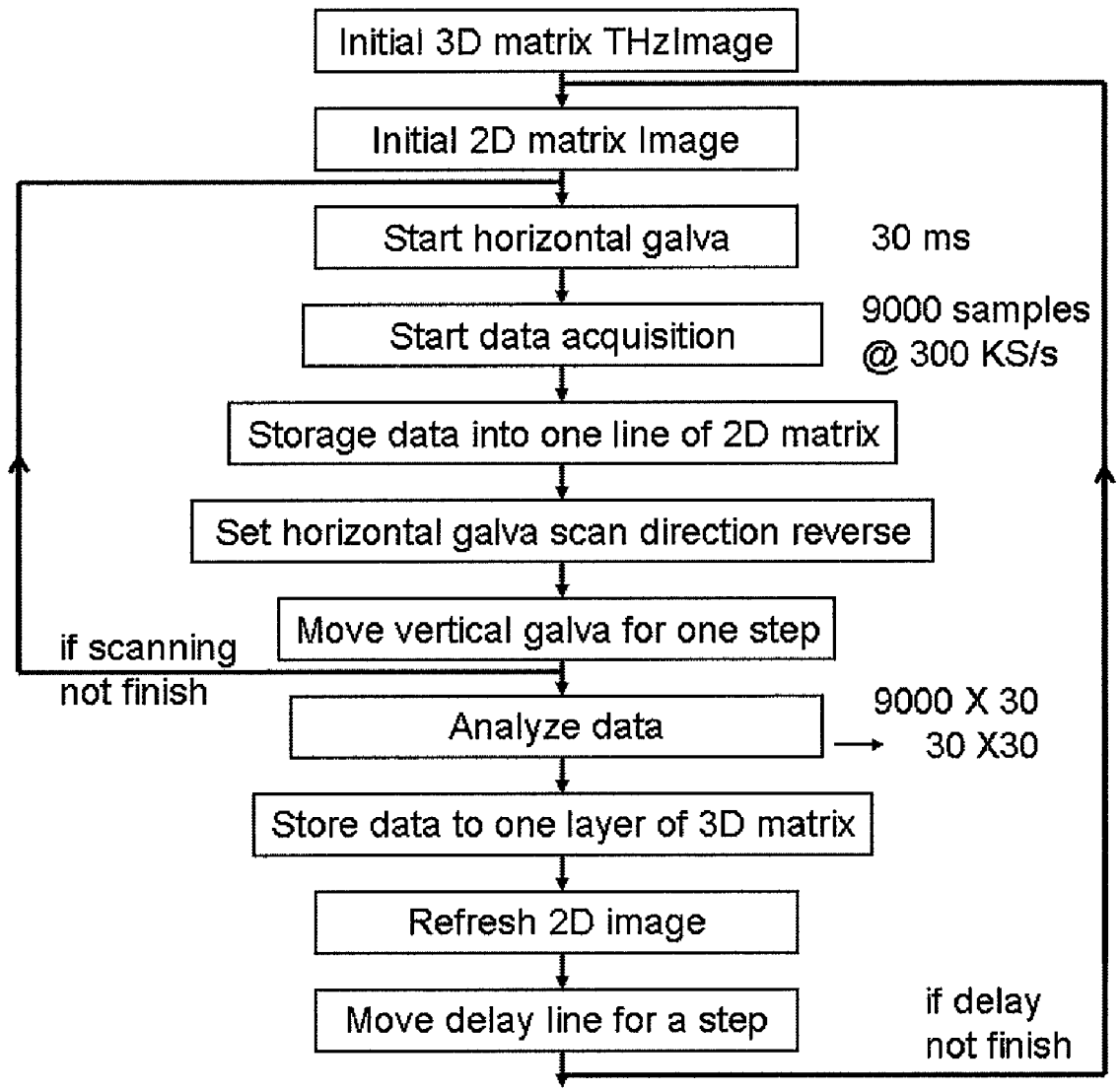
FIG. 12 shows a logic flow chart of the imaging process in the embodiment shown in FIG. 10.
Figure 13:
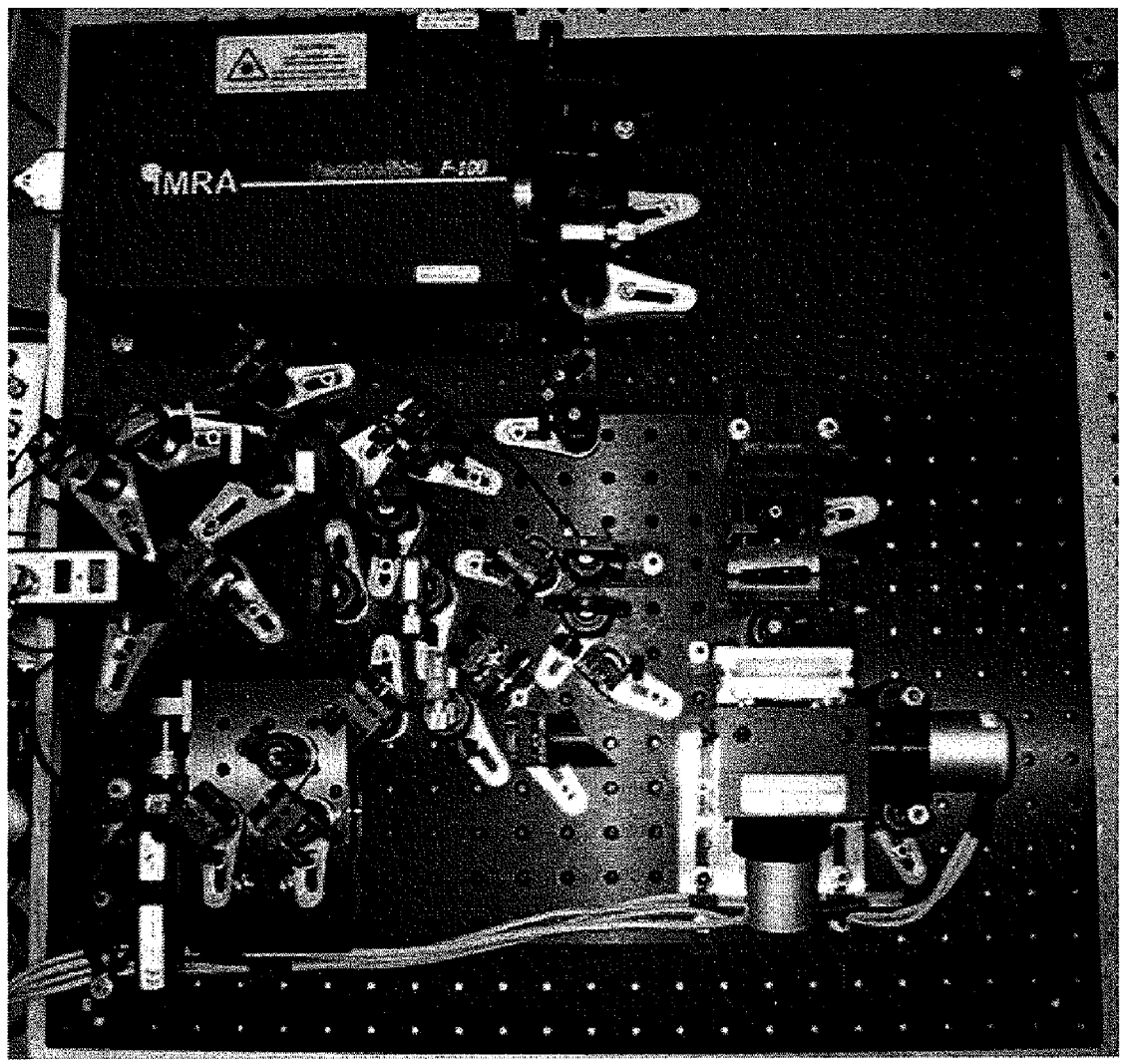
FIG. 13. is a photo of one embodiment of the invention used in a pulsed THz system.

FIG. 11 shows the concept of controlling geometry of the proof of concept system. To have high speed imaging, a high speed digital/analog multifunctional card with 600 KS/s data acquisition rate is used to acquire data and to control the scanning system. FIG. 12 shows a logic flow chart of the pulsed THz wave imaging process. FIG. 13 is a photo of this system.

Figure 14A:
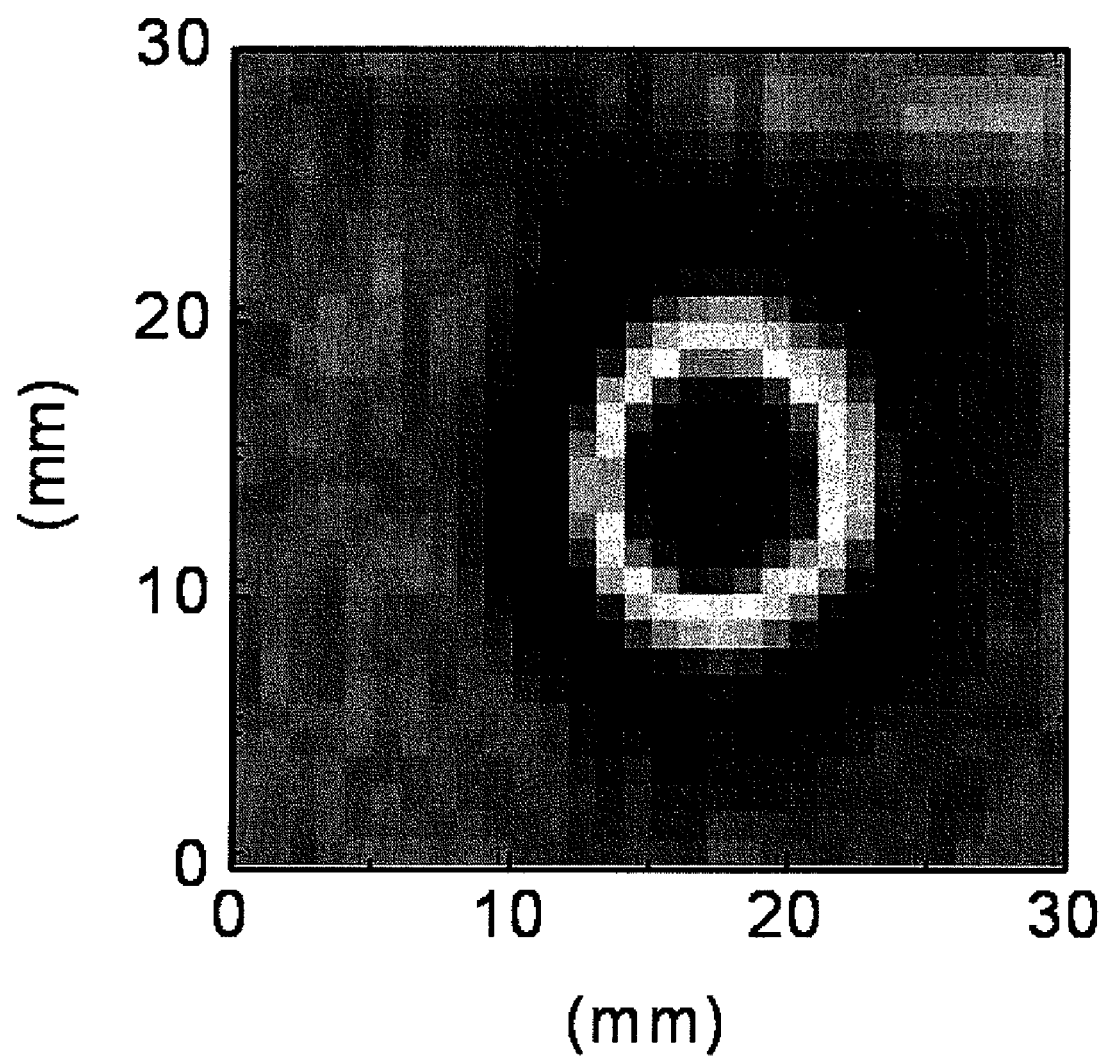
FIG. 14a shows THz field distribution in the image area at a fixed delay time.
Figure 14B:
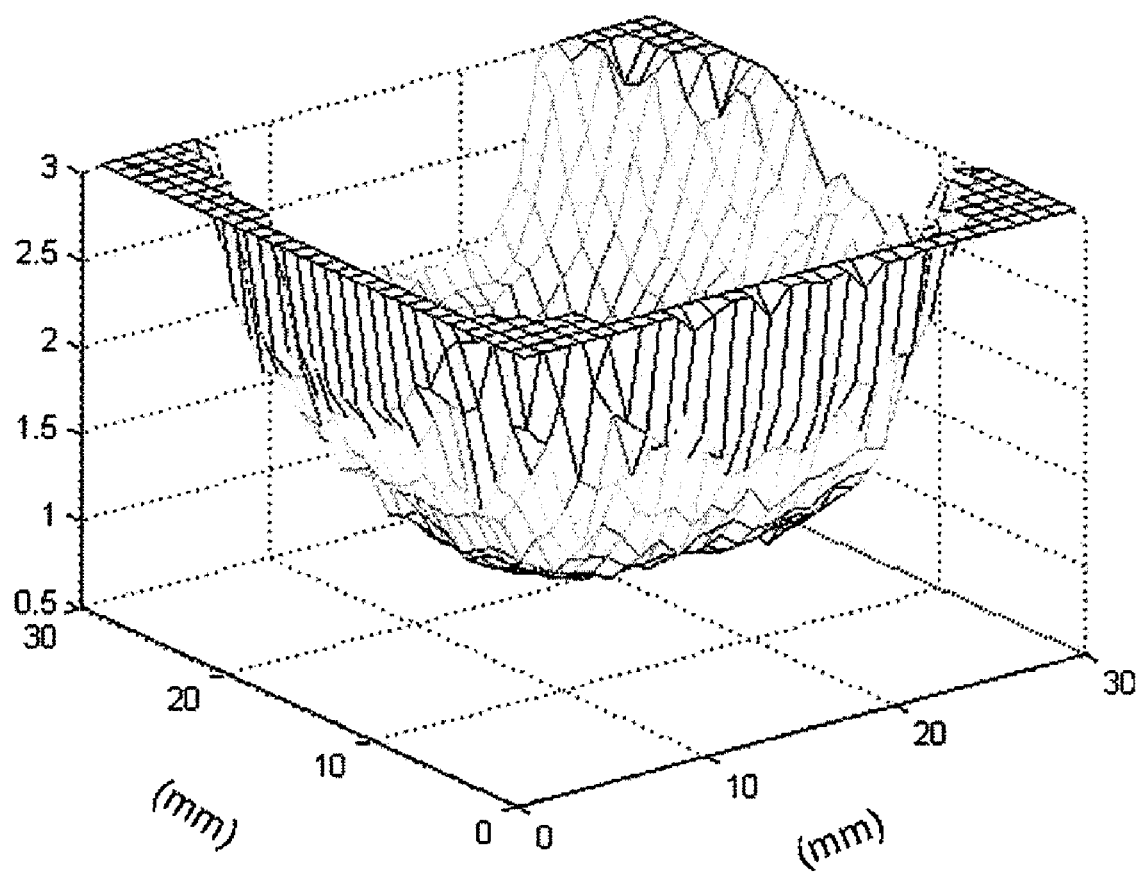
FIG. 14b shows THz amplitude distribution in image area.
Figure 14C:
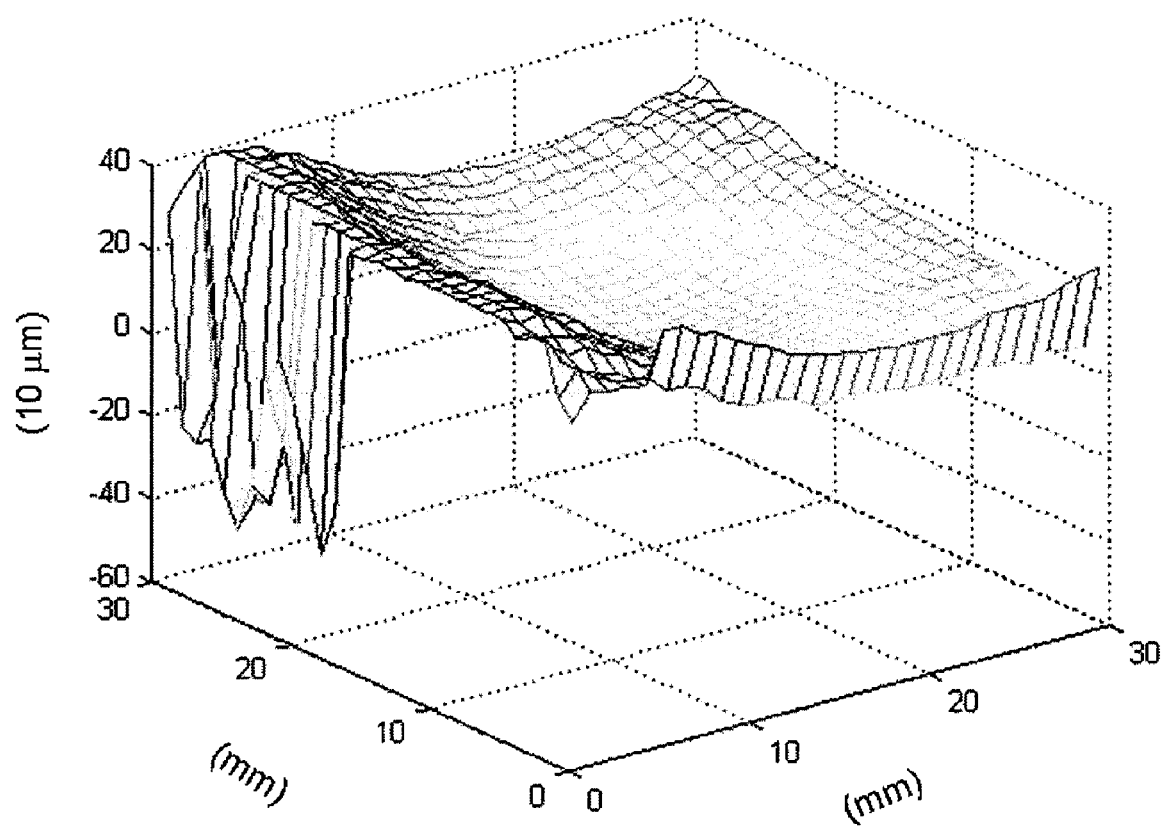
FIG. 14c is the distribution of THz pulses' peak timing in image area.
Figure 14D:
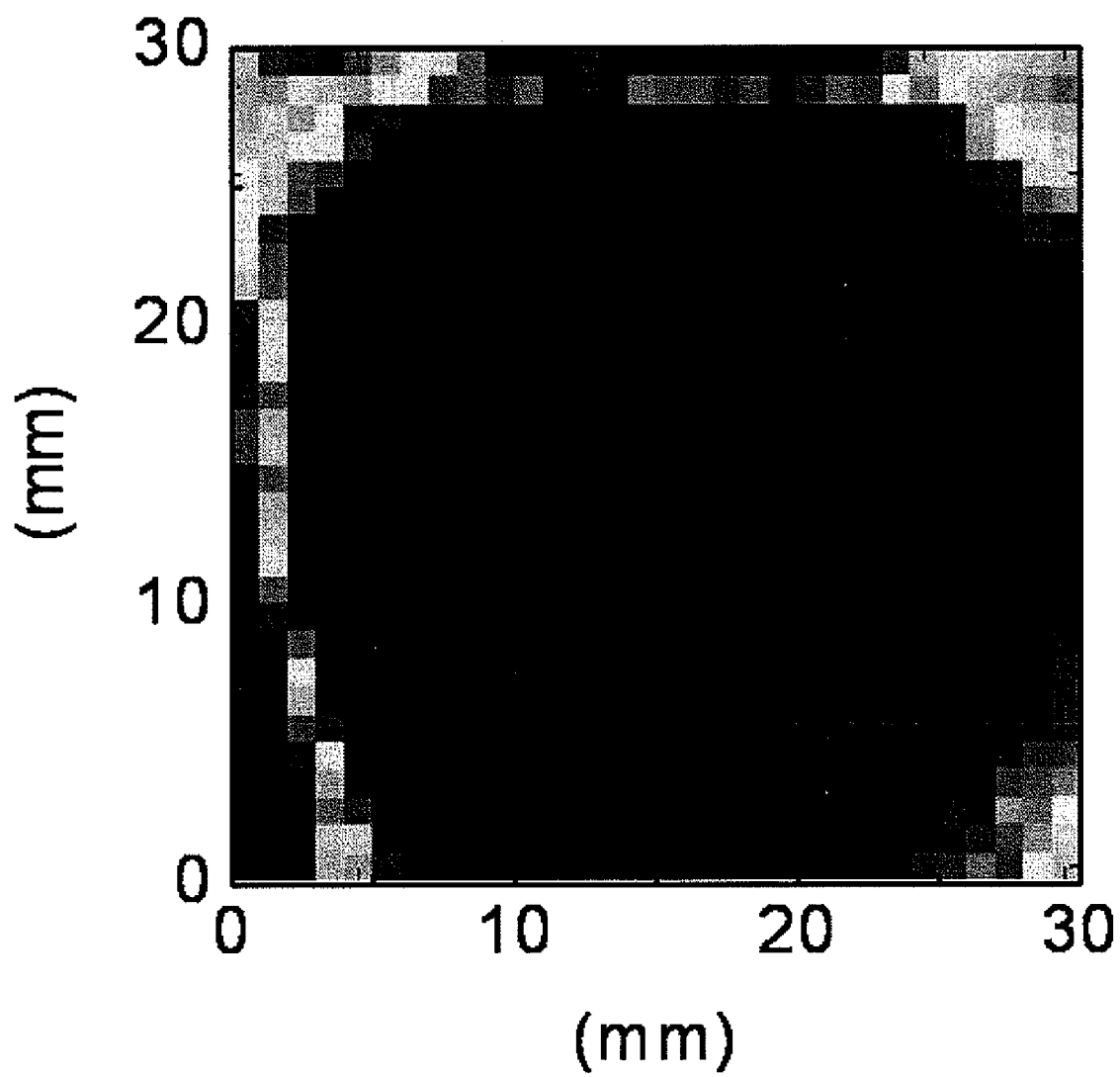
FIG. 14d shows calibrated distribution of THz amplitude in the image area.

FIG. 14a shows the distribution of THz field in the image area at a fixed delay time between pumping and probing pulses. The result was measured by using a metallic flat mirror as the target. Due to the temporal variation in scanning, the distribution of the THz field at a fixed timing shows ring structures like an interference pattern. FIG. 14b presents the distribution of THz amplitude (peak amplitude of THz waveform) in the image area. This figure gives a ratio of each pixel described as $A_0/A_i$, where $A_0$ is THz amplitude of the central pixel and $A_i$ indicates THz amplitude of the pixel whose index is i. FIG. 14c gives the temporal shift distribution in the image area comparing to the central pixel. Except for those pixels very close to the edge, the temporal variation in the entire range is about one THz wavelength. The distribution of THz field can be retrieved with images at all delay times. The retrieved THz field distribution is in FIG. 14d, which gives a uniform distribution except for those pixels very close to the edge.

Figure 15A:
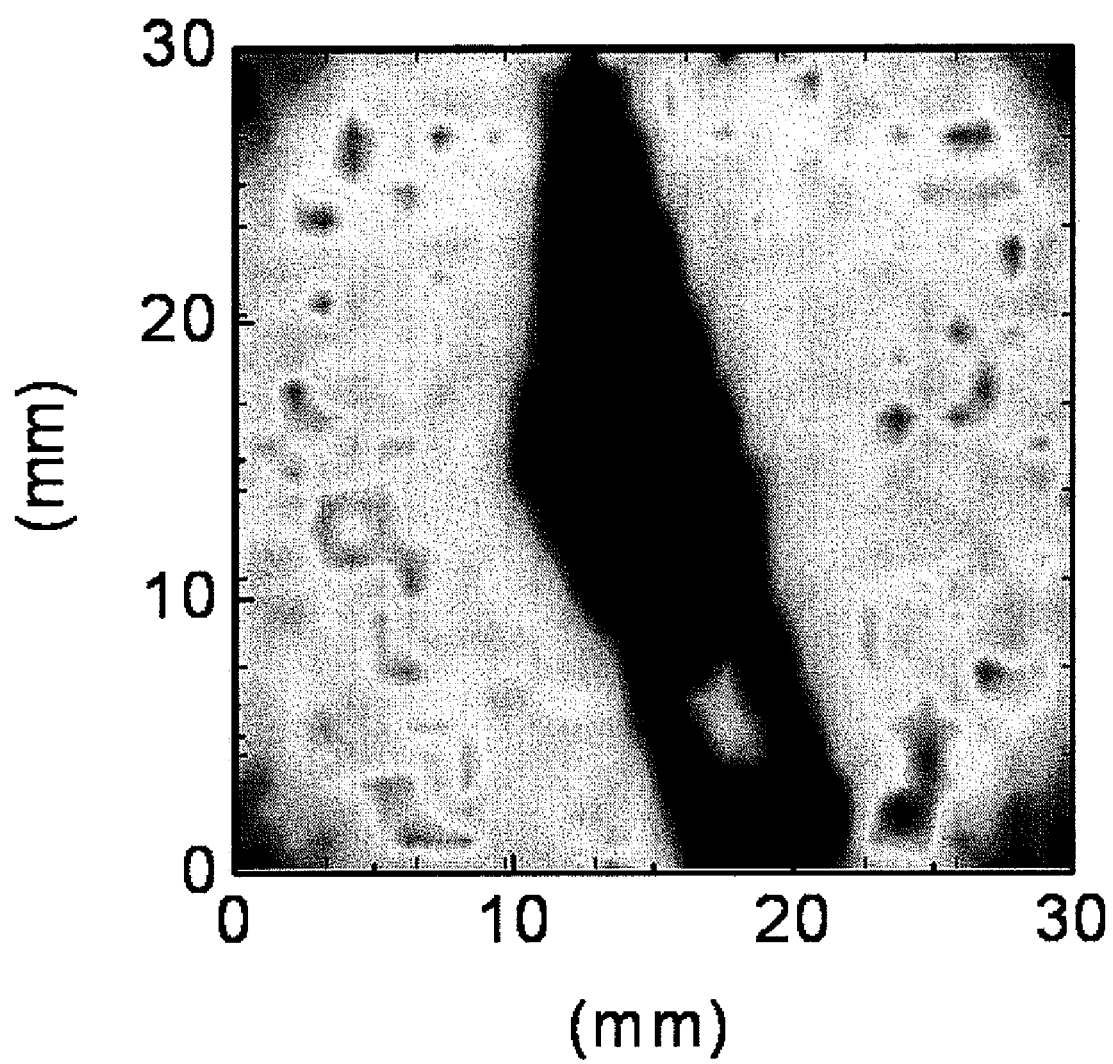
FIG. 15a gives a THz wave image of a metallic razor blade recorded according to the contrast to the background.
Figure 15B:
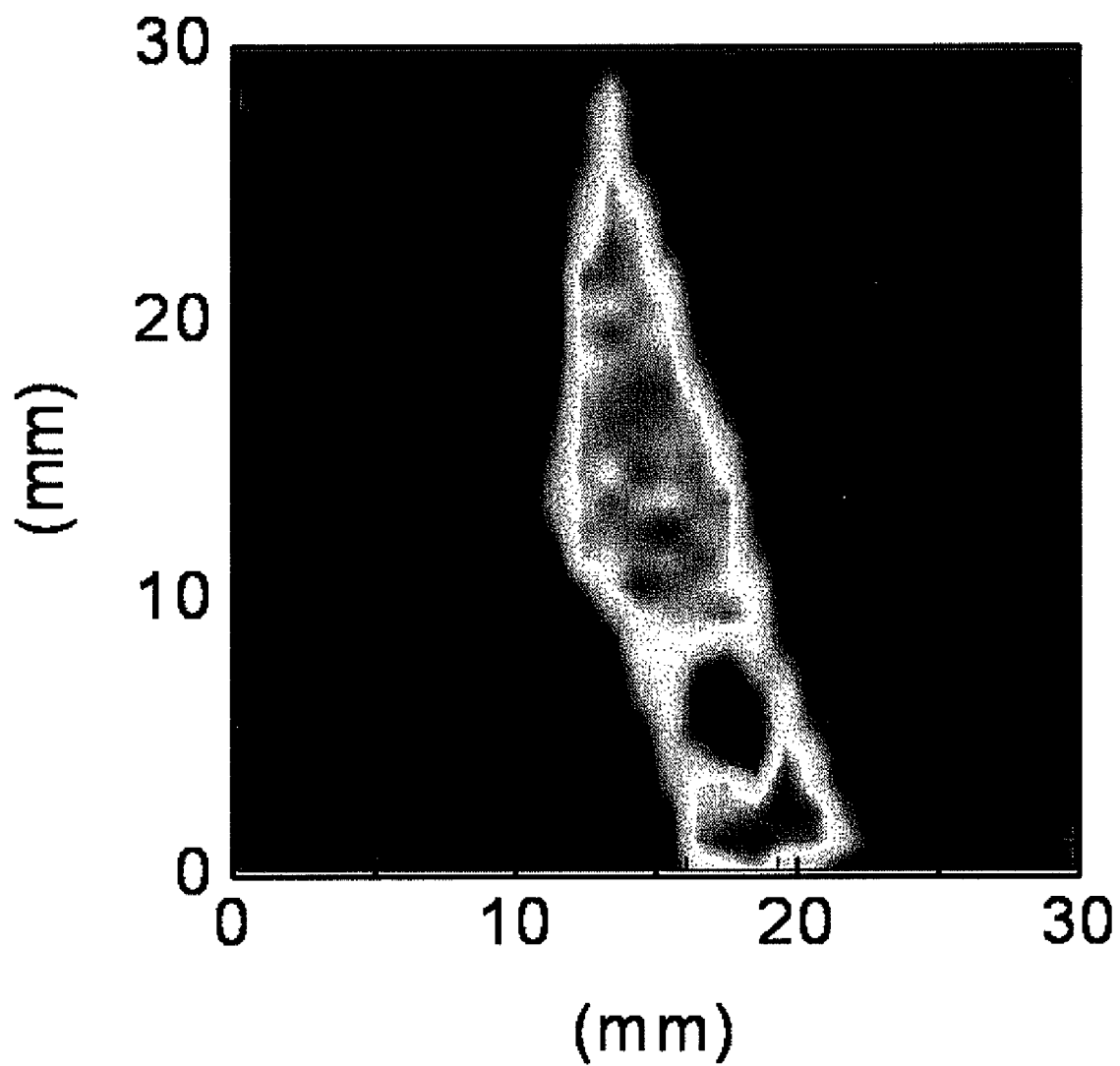
FIG. 15b is a THz wave image of the same blade using THz pulses reflected from its surface.
Figure 15C:
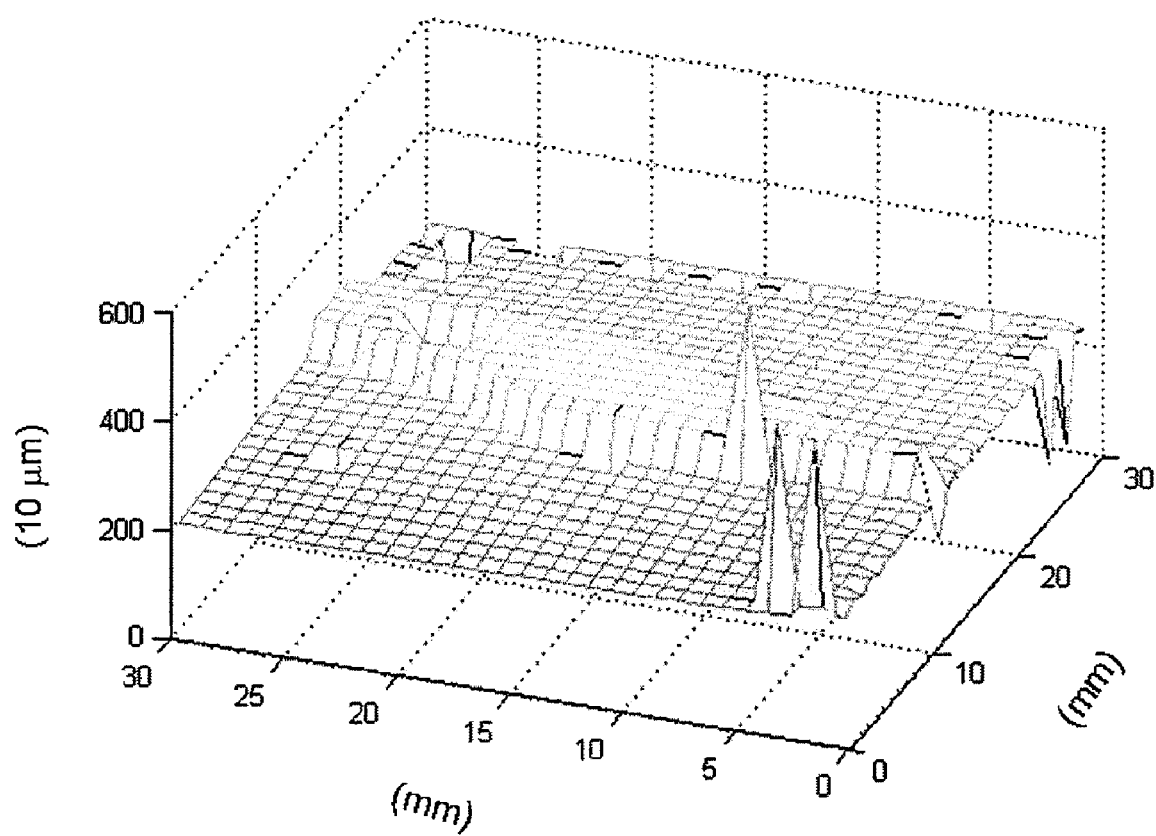
FIG. 15c gives a topographic image of the blade.

FIG. 15 show THz wave images of a metallic razor blade, which is mounted on top of the mirror. All images are recorded at a speed of 1 frame per second. FIG. 15a is an image recorded according to contrast to the background, which was caused due to the razor blade blocking THz radiation. FIG. 15b is an image of THz pulses reflected from the razor blade. FIG. 15c is a topographic image of the razor blade, which gives the thickness of the razor blade.

Figure 16A:
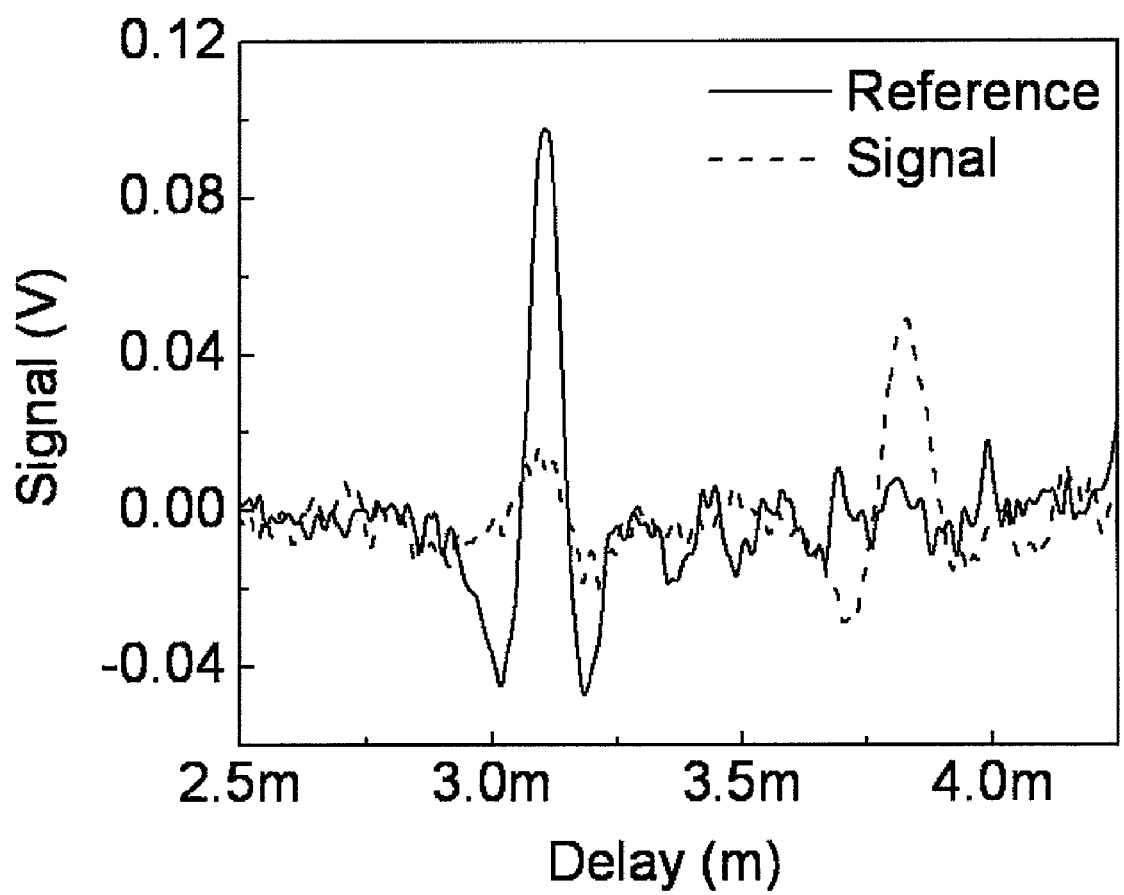
FIG. 16a compares THz waveforms with (dashed curve) and without (solid curve) target (a polyethylene pellet).
Figure 16B:
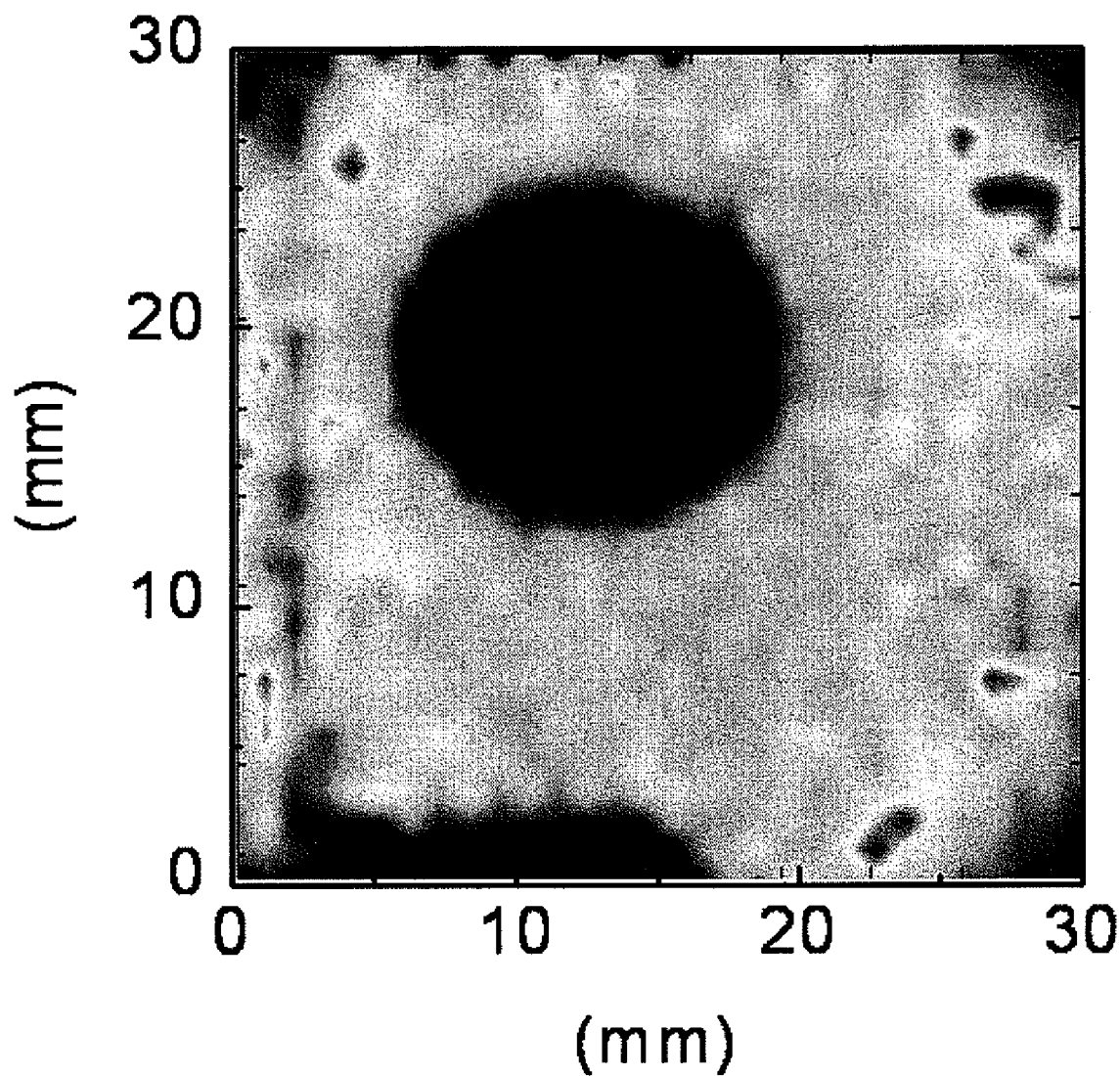
FIG. 16b is a THz wave image of this pellet recorded according to the contrast to the background.
Figure 16C:
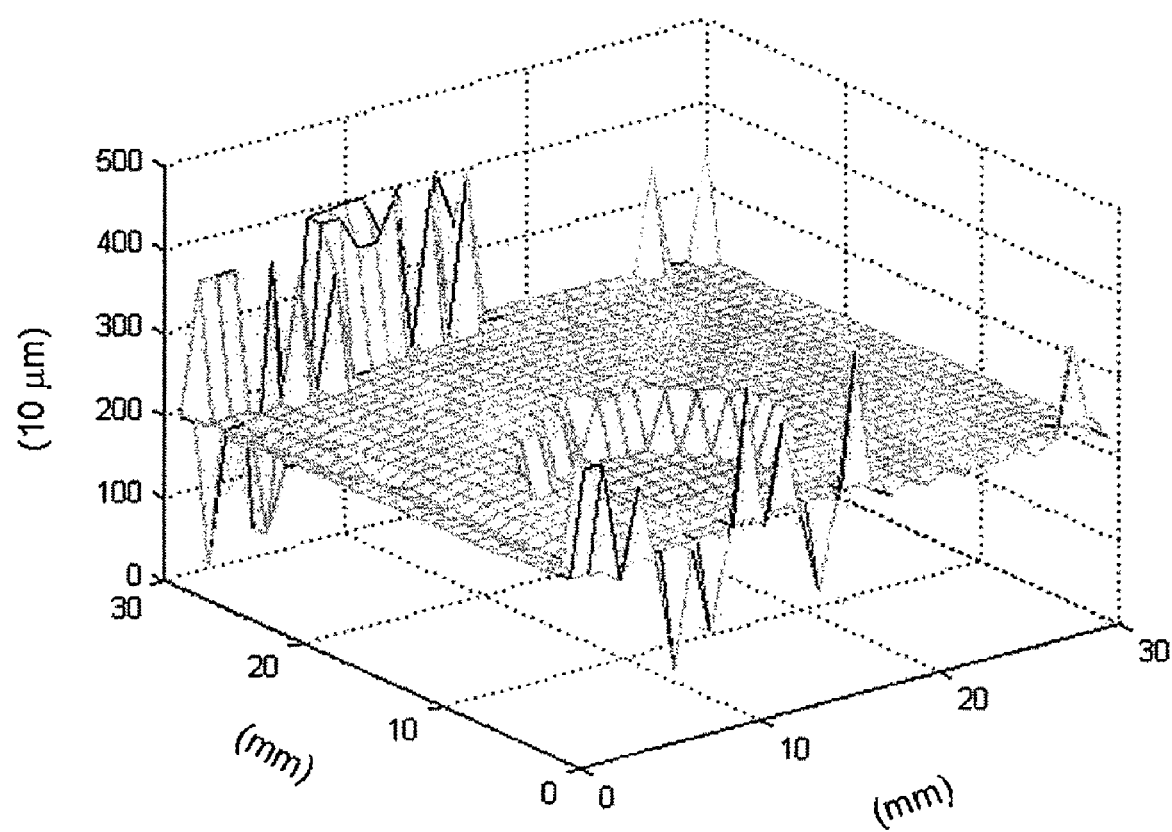
FIG. 16c is a topographic image of the pellet using the time delay of transmitted THz pulses.

THz wave imager was also used to image dielectric targets. FIG. 16a shows THz waveforms when there was (dashed curve) or was not (solid curve) a polyethylene pellet placed on the top of the metallic mirror. THz pulses transmitted through the target show a displacement along the delay axis. FIG. 16b shows a THz wave image of the pellet according to its contrast to the background, and FIG. 16c is a topographic image recorded according to time delay of THz pulses transmitted through the pellet.

Although the above discussion uses THz waves as imaging waves, embodiments of the invention may be utilize a frequency range of 1 GHz to 100 THz. Further, this technology can be applied to electromagnetic waves at other frequencies, sound, electron beams, et. al., which can be steered and focused, and can be used to image a target using this method.

What is claimed is:

1. An apparatus for imaging an area at extended THz frequencies, comprising:
   an electro-magnetic wave source generating a continuous wave or pulsed output, generated coherently or incoherently;
   steering optics for the electro-magnetic wave, the steering optics providing angular variation of the wave onto the focusing optics;
   an optical converter converting an angular variation of an incident wave into a lateral variation;
   focusing optics focusing the electro-magnetic wave at or within a target to be imaged;
   collecting optics collecting the electro-magnetic wave leaving the target;
   an electro-magnetic wave detector detecting the collected wave, a frequency range of the electro-magnetic wave being between 1 GHz to 100 THz,
   said steering optics and focusing optics being configured so that the wave is focused on a planar region, and in a normal direction to the region, over substantially the entire image area, the collecting optics being arranged to receive the wave to be imaged along one or both of a co-propagation and counter-propagation direction relative to the wave incident on the target over substantially the entire image area, and to deliver energy from at least a portion of the collected wave to the electro-magnetic wave detector during steering of the wave,
   at least a portion of said steering optics, focusing optics, and collecting optics comprising a beam path compensator to limit one or both of beam walking and temporal variation of an optical path during steering of the wave, said wave to be imaged carrying spectral information in reflection, transmission, scattering, refraction or diffraction arranged to the specular direction.

2. An apparatus as in claim 1, wherein the target emits the wave and is the wave source.

3. An apparatus as in claim 2, wherein an angular distribution of radiation of a point source located in the target is recorded for imaging.

4. An apparatus as in claim 3, wherein the steering optics further comprise: three galvanometers with three mirrors, first and second galvanometers and mirrors being used to scan the wave in one direction and a third galvanometer and mirror being used to scan the wave in another direction.

5. An apparatus as in claim 1, wherein the wave source and detector are not in the form of a multiple element array or an independently operating group of elements.

6. An apparatus as in claim 1, wherein the steering optics provides angular variation of an incident wave and comprises a single or multiple number of reflecting mirrors.

7. An apparatus as in claim 1, wherein the angular converter comprises a single or multiple number of lens or curved mirrors, or a combination of both.

8. An apparatus as in claim 1, wherein the focusing optics is a single or multiple number of lens or curved mirrors, or combination of both.

9. An apparatus as in claim 8, wherein the focusing and collecting optics are identical.

10. An apparatus as in claim 8, wherein the focusing, collecting and angular converting is performed by the same device.

11. An apparatus as in claim 1, wherein the collecting optics is a single or multiple number of lens or curved mirrors, or combination of both.

12. An apparatus as in claim 11, wherein the focusing and collecting optics are identical.

13. An apparatus as in claim 11, wherein the focusing, collecting and angular converting is performed by the same device.

14. An apparatus as in claim 1, wherein the collecting and focusing optics is identical and the optics moves relative to the target along with the optical axis of the optics, so that imaging of the target in the direction of the optical axis is achievable.

15. An apparatus as in claim 1, wherein the steering, angular converting, focusing, and collecting optics can be moved, so that a large-sized target can be imaged area-by-area.

16. An apparatus as in claim 1, wherein a beam splitter is used to pick up the wave out of the target.

17. An apparatus as in claim 1, wherein the optics or optical system before the detector comprises a focusing optic, which is used to focus the wave into a point detector.

18. An apparatus as in claim 1, wherein the transmitted wave through the target is recorded for imaging.

19. An apparatus as in claim 1, wherein the steering optics comprises mirrors mounted on galvanometers or rotational mirrors, or a combination of both.

20. An apparatus as in claim 1, wherein the focusing optics comprise two cylindrical lenses configured to minimize parallel beam walking and the temporal variation in the imaging process.

21. An apparatus as in claim 1, wherein the focusing optics comprise a single optic or an optical set, wherein focal lengths along two different axes are different in order to minimize parallel beam walking and temporal variation in the imaging process.

22. An apparatus as in claim 1, wherein the steering optics comprise a steering mirror having a small displacement to the focal spot of the focusing or collecting lens.

23. An apparatus as in claim 1, wherein the wave from the source is not collimated and adjustment is required to optimize the wave out of target to the detector.

24. An apparatus as in claim 1, wherein the steering optics comprise steering mirrors, wherein the steering mirrors are synchronized to each other, so that the wave after the steering optics maintains a fixed direction.

25. An apparatus as in claim 1, wherein phase sensitive coherent detection of the wave is used in the time domain.

26. An apparatus as in claim 24, wherein spectral imaging is achieved by the time domain measurement.

27. An apparatus as in claim 1, wherein the wave is generated by using a laser light source.

28. An apparatus as in claim 1, wherein the collected information from imaging is processed by controlling all active devices in the imaging system.

29. An apparatus as in claim 1, wherein the frequency range is up to about 20 THz.

30. An apparatus as in claim 1, wherein focusing optics comprise a parabolic mirror, and the parabolic mirror is configured to transmit and receive THz waves.

31. An apparatus as in claim 1, wherein a frequency range of said electro-magnetic wave is in the range from about 10 GHz to 10 THz.

32. An apparatus as in claim 1, said apparatus comprising:
steering optics disposed at opposite sides to each other with respect to a plane of the target, a portion of the steering optics directing the electromagnetic wave to the target, and a portion of said steering optics on the opposite side with respect to the plane of the target collecting the wave to be imaged.

33. An apparatus for imaging an area at extended THz frequencies, comprising: an electro-magnetic wave source generating a continuous wave or pulsed output, generated coherently or incoherently,
steering optics for the electro-magnetic wave, the steering optics providing angular variation of the wave onto the focusing optics;
an optical converter converting an angular variation of an incident wave into a lateral variation;
focusing optics focusing the electro-magnetic wave at or within a target to be imaged;
collecting optics collecting the electro-magnetic wave leaving the target;
an electro-magnetic wave detector detecting the collected wave, a frequency range of the electro-magnetic wave being between 1 GHz to 100 THz, said steering optics and focusing optics being configured so that the wave is focused on a planar region, and in a normal direction to the region, over substantially the entire image area, the collecting optics being arranged to receive the wave to be imaged along one or both of a co-propagation and counter-propagation direction relative to the wave incident on the target over substantially the entire image area, and to deliver energy from at least a portion of the collected wave to the electro-magnetic wave detector during steering of the wave, said wave to be imaged carrying spectral information in reflection, transmission, scattering, refraction or diffraction arranged to the specular direction,
wherein the target emits the wave and is the wave source, an angular distribution of radiation of a point source located in the target is recorded for imaging, and the steering optics further comprises: three galvanometers with three mirrors, first and second galvanometers and mirrors being used to scan the wave in one direction and a third galvanometer and mirror being used to scan the wave in another direction.

* * * * *